(12) United States Patent
Brady et al.

(10) Patent No.: US 8,123,778 B2
(45) Date of Patent: Feb. 28, 2012

(54) EMBOLIC PROTECTION SYSTEM

(75) Inventors: Eamon Brady, Elphin (IE); Gary Fahey, Rosscahill (IE); Brendan Casey, Barna (IE); Ann Marie Cannon, Pettigo (IE); David Vale, Clontarf (IE); Martin Keegan, Knocknacarra (IE)

(73) Assignee: Salviac Limited, Dublin (IE)

( * ) Notice: Subject to any disclaimer, the term of this patent is extended or adjusted under 35 U.S.C. 154(b) by 428 days.

(21) Appl. No.: 12/259,700

(22) Filed: Oct. 28, 2008

(65) Prior Publication Data

US 2009/0254115 A1     Oct. 8, 2009

Related U.S. Application Data

(63) Continuation of application No. 10/435,661, filed on May 12, 2003, now abandoned.

(60) Provisional application No. 60/378,958, filed on May 10, 2002.

(51) Int. Cl.
*A61M 29/00* (2006.01)
(52) U.S. Cl. .................................................. 606/200
(58) Field of Classification Search .................. 606/200, 606/108, 110, 113, 114, 127, 159, 191–194; 206/363, 364, 438, 439
See application file for complete search history.

(56) References Cited

U.S. PATENT DOCUMENTS

| | | |
|---|---|---|
| 4,425,908 A | 1/1984 | Simon |
| 5,152,777 A | 10/1992 | Goldberg et al. |
| 5,397,310 A | 3/1995 | Chu et al. |
| 5,549,626 A | 8/1996 | Miller et al. |
| 5,755,709 A | 5/1998 | Cuppy |
| 5,800,525 A | 9/1998 | Bachinski et al. |
| 5,957,892 A | 9/1999 | Thorne |
| 6,168,579 B1 | 1/2001 | Tsugita |
| 6,277,139 B1 | 8/2001 | Levinson et al. |
| 6,336,934 B1 | 1/2002 | Gilson et al. |
| 6,395,014 B1 | 5/2002 | Macoviak et al. |
| 6,461,665 B1 | 10/2002 | Scholander |
| 6,485,501 B1 * | 11/2002 | Green ........................... 606/200 |
| 6,565,591 B2 | 5/2003 | Brady et al. |
| 6,752,819 B1 | 6/2004 | Brady et al. |
| 6,848,574 B1 | 2/2005 | Israelsson et al. |
| 6,869,938 B1 * | 3/2005 | Schwartz et al. ............... 514/57 |
| 6,887,256 B2 | 5/2005 | Gilson et al. |
| 2002/0049467 A1 | 4/2002 | Gilson et al. |
| 2002/0052626 A1 | 5/2002 | Gilson et al. |

FOREIGN PATENT DOCUMENTS

| | | | |
|---|---|---|---|
| IE | WO 00/67670 | * | 11/2000 |
| WO | 99/51167 A2 | | 10/1999 |
| WO | 01/97714 A1 | | 12/2001 |

* cited by examiner

*Primary Examiner* — Elizabeth Houston
(74) *Attorney, Agent, or Firm* — Sughrue Mion, PLLC; Jonathan Feuchtwang

(57) ABSTRACT

An embolic protection system comprises an embolic protection filter 1 having a collapsed delivery configuration and an expanded deployed configuration. The filter 1 is housed in the collapsed configuration in a reception space of a delivery catheter 20. The delivery catheter 20 containing the filter 1 is housed in a sealed sterile pouch 35. The filter 1 may be coated with a non-thrombogenic coating and an adhesion preventer 9 such as a silicon gel is used to substantially prevent adhesion of adjacent folds of the filter 1 when the filter is in the collapsed configuration in the delivery catheter 20.

39 Claims, 21 Drawing Sheets

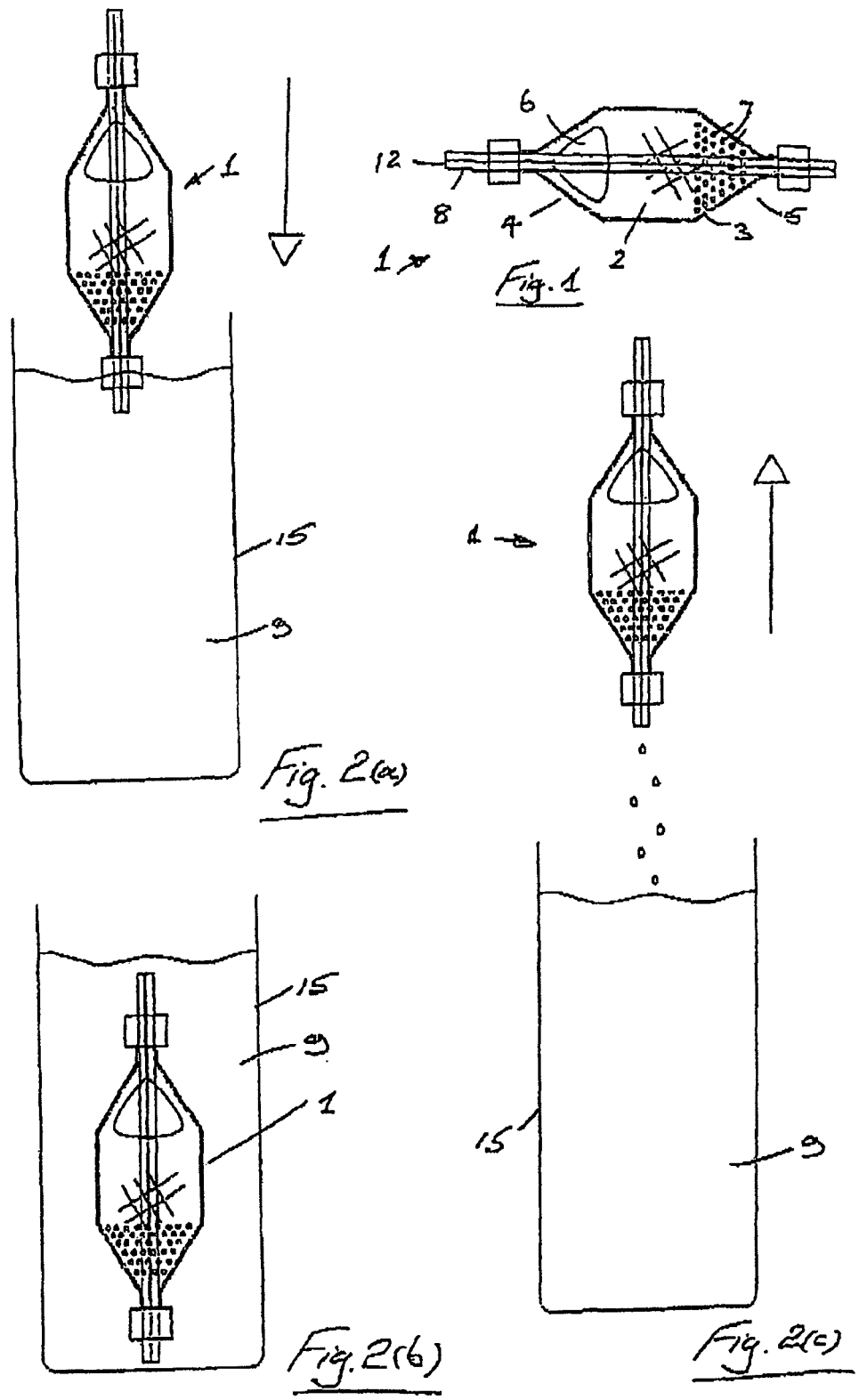

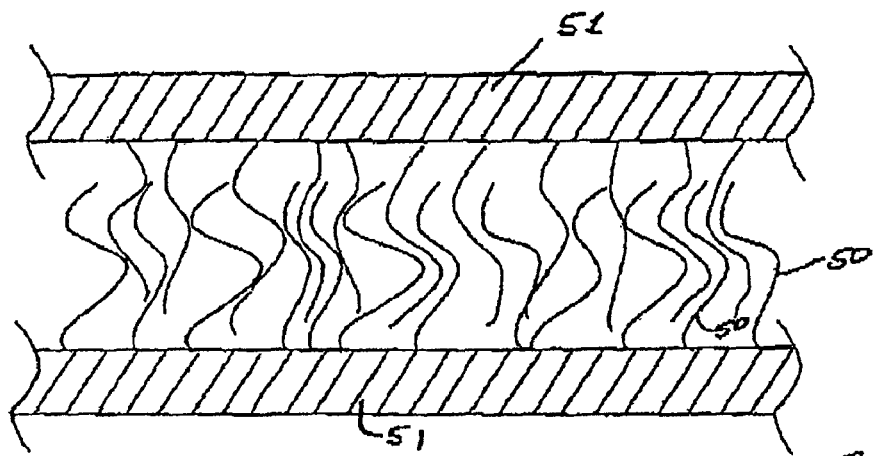
Fig. 7
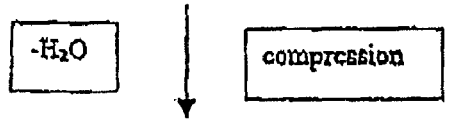
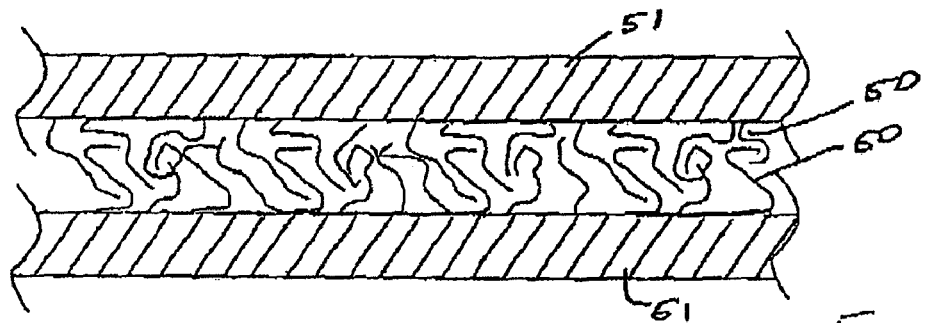
Fig. 9
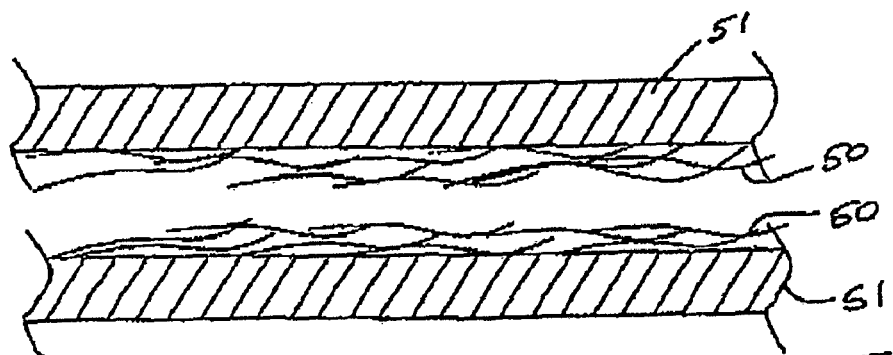
Fig. 8

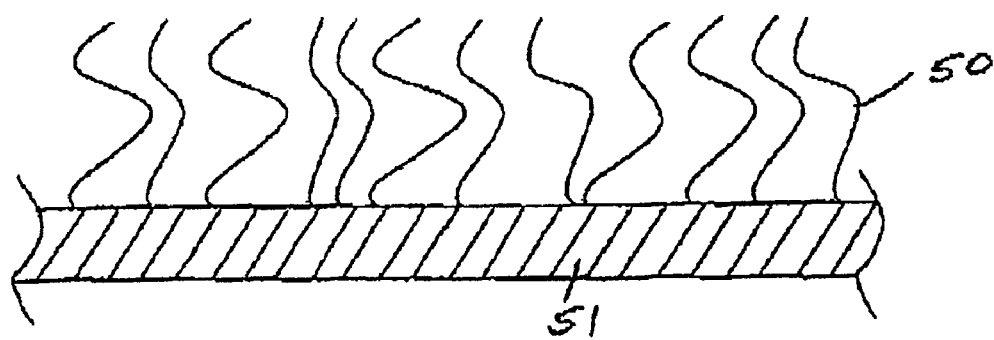
Fig. 11
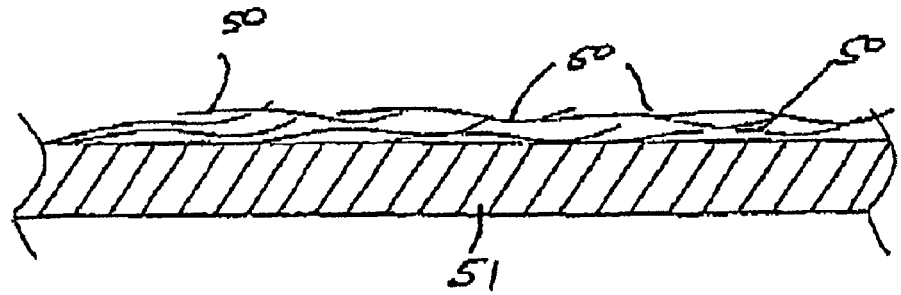
Fig. 10

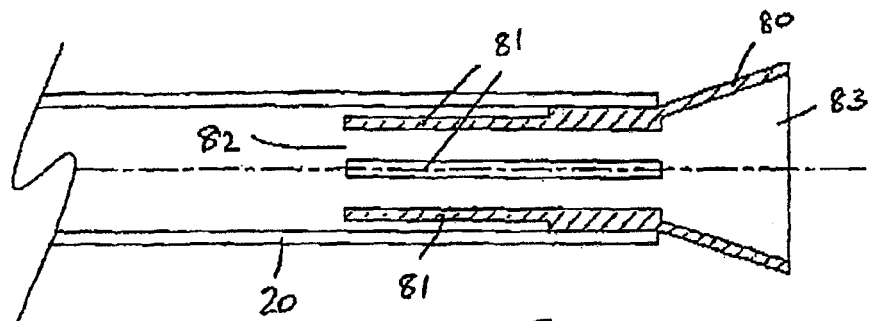
Fig. 22
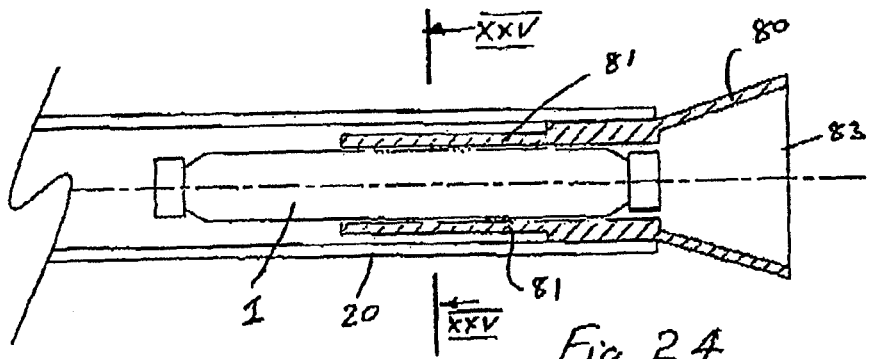
Fig. 24
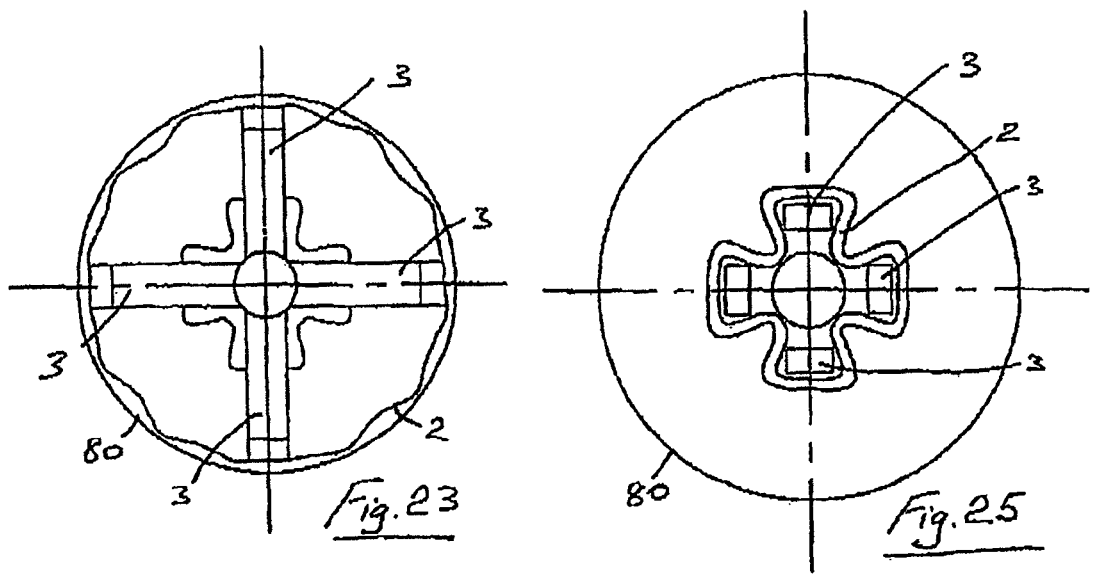
Fig. 23
Fig. 25

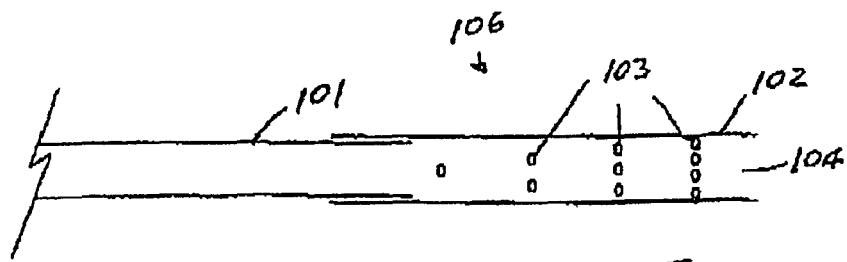
Fig. 29
Fig. 30
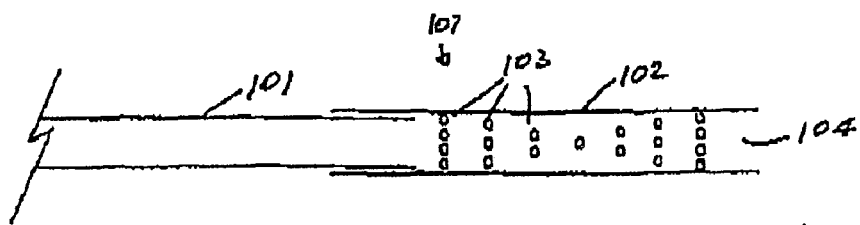
Fig. 31
Fig. 32
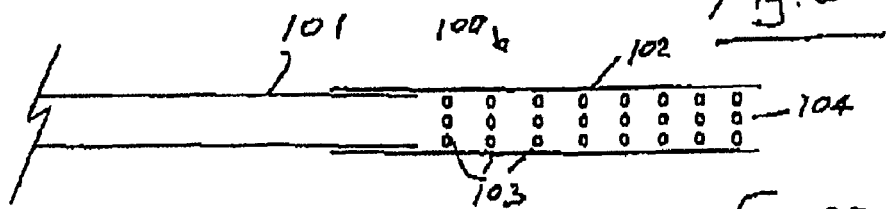
Fig. 27
Fig. 28

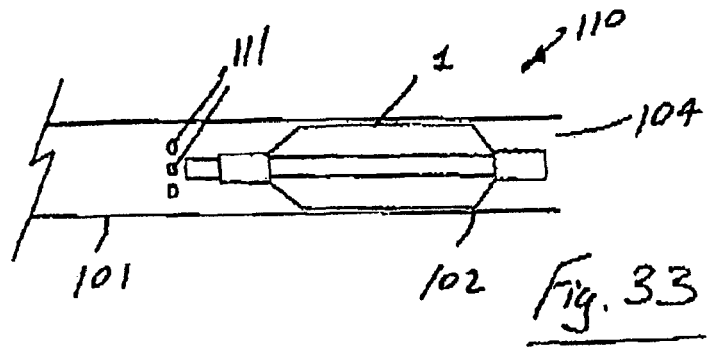
Fig. 33
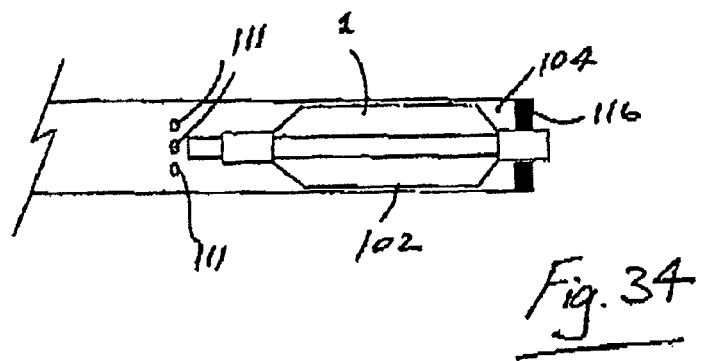
Fig. 34
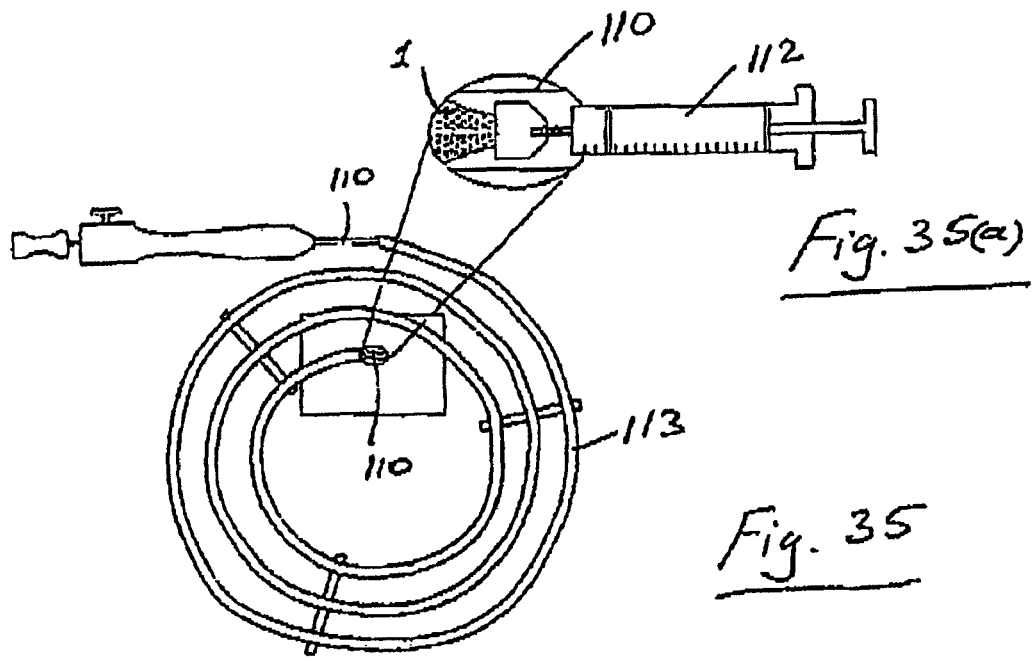
Fig. 35(a)
Fig. 35

EMBOLIC PROTECTION SYSTEM

This application is a continuation of Ser. No. 10/435,661 filed May 12, 2003, now abandoned, which claims benefit of priority under 35 U.S.C. §119(e) to U.S. Provisional Patent Application No. 60/378,958, filed May 10, 2002, and all of the disclosures of which are hereby incorporated by reference in their entirety.

BACKGROUND OF THE INVENTION

This invention relates to an embolic protection filter, which is movable between a collapsed configuration for transport through a vasculature and an expanded configuration for deployment in a vasculature.

It is known to collapse down and load an embolic protection filter into a delivery catheter. The collapsed filter may then be transported through a vasculature using the delivery catheter until the filter is located at a desired site in the vasculature where the filter may be deployed out of the delivery catheter.

It is also known to coat embolic protection filters with a biocompatible coating to minimize the risk of fibrin build-up on the filter, and the risk of clots forming in the blood stream. Many of these biocompatible coatings have hydrophilic properties. These hydrophilic coatings interact with water molecules. Water molecules may be absorbed during manufacture, sterilization, storage or in use. Often the quantity of water absorbed is low leading to the biocompatible coating swelling slightly, and the coating becoming sticky or tacky.

Filter membranes in this state have the potential for self-adherence and this can lead to the collapsed filter becoming stuck to itself in the collapsed configuration with the result that the filter will fail to expand fully, or even expand at all, when deployed in the vasculature. Failure of an embolic protection filter to correctly deploy in a vasculature can potentially lead to embolic material migrating downstream through the vascular system with potentially life-threatening consequences.

Another problem which arises with a low profile filter loaded into a catheter pod is the difficulty in successfully flushing the device to remove any air. Because the filter assumes a packed configuration in the pod it is difficult to remove air from the filter. It may also be easier for the filter to remove itself from the pod due to the flushing pressure in preference to the filter being flushed of air.

This invention is therefore aimed at overcoming at least some of the problems associated with known embolic protection systems.

STATEMENTS OF INVENTION

An embolic protection system comprising:
  an embolic protection filter having a collapsed delivery configuration and an expanded deployed configuration;
  a delivery catheter having a reception space, an embolic protection filter being housed in the collapsed configuration in the reception space of the delivery catheter; and
  a sealed sterile pouch housing the delivery catheter containing the filter in the collapsed configuration.

In one embodiment the filter in the collapsed configuration is at least partially folded.

In another embodiment the system comprises an adhesion preventer to substantially prevent adhesion of adjacent folds of the filter to one another in the collapsed configuration.

In a further embodiment the adhesion preventing material is selected from one or more of:
  a silicon fluid;
  a silicon gel;
  a lipid filled fluid/gel;
  a heparin filled fluid/gel; and
  an aqueous solution.

The invention also provides a medical device movable between a collapsed configuration for transport through a vasculature and an expanded configuration for deployment in a vasculature:
  the device having a collapsed configuration in which the device is at least partially folded and an expanded configuration: and
  the device comprising an adhesion preventer to prevent adhesion of adjacent folds of the device in the collapsed configuration to one another.

In a preferred embodiment the device comprises a collapsible body and a support structure to support the body in the expanded configuration. The collapsible body may be located at least partially externally of the support structure. The support structure may be located at least partially externally of the collapsible body.

In one embodiment the adhesion preventer comprises means to space adjacent folds of the device apart. Preferably the means to space adjacent folds of the device apart comprises a filler material applied to a surface of the device. The filler material may comprise a silicon fluid, or a silicon gel, or a lipid filled fluid/gel, or a heparin filled fluid/gel, or an aqueous material.

In one case the means to space adjacent folds of the device apart comprises one or more arms for extending between adjacent folds of the device. The support structure may comprise the arm. In a preferred embodiment the arm is provided by a tool which is suitable to assist loading of the device into a catheter.

Preferably the biocompatible surface is provided as a coating of biocompatible material on the device.

The biocompatible surface may be provided on an external surface of the device.

The biocompatible surface may be provided on an internal surface of the device.

According to another aspect the invention provides a method for providing embolic protection during a vascular procedure comprising the steps of:
  providing an embolic protection system comprising a sealed sterile pouch containing a delivery catheter with a reception space, an embolic protection filter being housed in the reception space in collapsed configuration;
  opening the pouch; and
  removing the delivery catheter containing the embolic protection filter in the collapsed configuration from the pouch.

In one embodiment the method comprises the step of flushing the filter in the collapsed configuration within the delivery catheter.

In another embodiment the filter is flushed prior to sealing of the pouch.

In another aspect of the invention, there is provided a medical device movable between a collapsed configuration for transport through a vasculature and an expanded configuration for deployment in a vasculature, the device comprising:
  a storage space for storing a biocompatible material during transport through a vasculature; and
  means to deliver the biocompatible material from the storage space to a surface of the device when deployed in a vasculature.

The storage space may be provided in a wall of the device.

Preferably the means to deliver the biocompatible material comprises one or more channels from the storage space to the surface of the device. Ideally the channel is a capillary channel.

In one case the biocompatible material is delivered to an external surface of the device. In another case the biocompatible material is delivered to an internal surface of the device.

In a preferred embodiment the device comprises a delivery actuator to at least partially cause delivery of the biocompatible material from the storage space to the surface of the device. Ideally the actuator is at least partially of a temperature memory material.

The biocompatible material may be a hydrophilic material.

In one preferred case the device is an embolic protection filter. Ideally the filter has an inlet end and an outlet end, the inlet end having one or more inlet openings sized to allow blood and embolic material enter the filter, the outlet end having a plurality of outlet openings sized to allow through passage of blood but to retain undesired embolic material within the filter.

In a further aspect, the invention provides a method of loading a medical device into a catheter, the method comprising the steps of:
    collapsing the medical device down to a wrapped configuration;
    controlling the wrap of the medical device during collapse; and
    positioning the medical device at least partially within the catheter.

The medical device may be at least partially collapsed down by passing the medical device through a funnel. Preferably the wrap of the medical device is at least partially controlled by formations on the funnel.

In another embodiment the medical device is at least partially collapsed down by directing a jet of fluid over the medical device. Ideally the wrap of the medical device is at least partially controlled by directing a jet of fluid over the medical device.

Most preferably the medical device is at least partially collapsed during positioning of the medical device at least partially within the catheter.

According to another aspect of the invention, there is provided a system for loading a medical device into a catheter, the system comprising:
    means to collapse a medical device down to a wrapped configuration; and
    means to control the wrap of the medical device.

In one embodiment the means to collapse comprises a funnel through which a medical device may be passed. Preferably the means to control the wrap comprises one or more formations on the funnel. Ideally the formation comprises an inward protrusion on a wall of the funnel. The protrusion may be in the form of a finger extending from an end of the funnel. Preferably the finger extends generally longitudinally. The finger may extend generally in a spiral. Most preferably the finger extends from an outlet end of the funnel. Ideally the system comprises four fingers spaced-apart around the circumference of the funnel. The fingers are preferably equi-spaced apart.

In another embodiment the means to collapse comprises one or more fluid jets for directing a jet of fluid over the medical device. The means to control the wrap may comprise one or more fluid jets for directing a jet of fluid over the medical device.

The invention provides in a further aspect a method of loading a medical device into a catheter, the method comprising the steps of:
    collapsing the medical device;
    positioning the collapsed medical device at least partially within the catheter; and
    flushing a liquid through the catheter and the collapsed medical device.

The method may comprise the step of sealing the catheter with flushing liquid therein.

In another aspect of the invention, there is provided a method of delivering a medical device to a desired location in a vasculature, the method comprising the steps of:
    providing a catheter with a collapsed medical device positioned at least partially within the catheter;
    flushing a liquid through the catheter and the collapsed medical device; and
    introducing the catheter into a vasculature and advancing the catheter through the vasculature.

Preferably the method comprises the step of monitoring the extent to which the collapsed medical device has been flushed. Ideally the flushing step is terminated when the collapsed medical device has been fully flushed.

The liquid may be flushed distally through the catheter. The liquid may be flushed proximally through the catheter.

Desirably the liquid is flushed through the catheter by creating a pressure differential across the collapsed medical device.

In a further aspect, the invention provides a catheter having a reception space at a distal end of the catheter for receiving a collapsed medical device therein, a wall of the catheter around the reception space having flushing openings through the wall to facilitate flushing of a collapsed medical device in the reception space.

The concentration of the flushing openings may increase distally along the reception space. The concentration of the flushing openings may increase proximally along the reception space. The concentration of the flushing openings may increase from a centre of the reception space towards proximal and distal ends of the reception space.

The catheter preferably comprises means to indicate the extent of flushing of the reception space. Ideally the means to indicate comprises one or more perfusion openings in the catheter wall at an end of the reception space.

The means to indicate may be provided by a separate component. Preferably the means to indicate is provided by a stylet extendable through the catheter.

In one case the means to indicate comprises an element configured to change color upon contact with a flushing liquid. Preferably the element comprises litmus.

In a preferred embodiment the catheter comprises a seal for sealing the reception space with a collapsed medical device and flushing liquid therein. The seal may extend along substantially the full length of the catheter.

The invention provides in another aspect a catheter assembly comprising a catheter of the invention and a collapsible medical device receivable in the reception space of the catheter, the medical device having one or more flushing openings in a body of the medical device to facilitate flushing of the medical device when collapsed in the reception space.

Preferably the medical device body comprises a coiled spring.

According to another aspect of the invention, there is provided a catheter assembly comprising:
    a catheter having a reception space at a distal end of the catheter for receiving a collapsed medical device therein; and means for reinforcing against creep a wall of the catheter around the reception space.

In one case the means for reinforcing reinforce the catheter wall against longitudinal creep. In another case the means for reinforcing reinforce the catheter wall against radial creep.

In a preferred embodiment the means for reinforcing comprises a clamp for positioning around the catheter wall. The clamp may comprise a sleeve.

In another case the assembly comprises a tray for the catheter, and the clamp is provided by the tray.

Ideally the clamp is configured to provide non-uniform reinforcement along the catheter wall. Most preferably the clamp comprises one or more formations to provide non-uniform reinforcement along the catheter wall.

In another embodiment the means for reinforcing comprises one or more reinforcing elements in the catheter wall. Preferably the catheter wall is of a composite construction.

In a further aspect, the invention provides a catheter assembly comprising:
  a catheter having a reception space at a distal end of the catheter for receiving a collapsed medical device therein; and
  means for elongating a medical device received in the reception space to resist creeping of the medical device.

The means for elongating may comprise a tensioning wire attachable to a medical device.

The invention provides in another aspect a method of loading a medical device into a catheter, the method comprising the steps of:
  collapsing the medical device;
  positioning the collapsed medical device at least partially within the catheter; and
  applying pressure to the catheter and/or to the collapsed medical device to distribute loading stresses on the catheter and/or on the collapsed medical device.

The pressure is preferably applied longitudinally.

The pressure may be applied radially.

In one case the applied pressure is substantially constant over time. In another case the applied pressure varies over time. Ideally the applied pressure varies cyclically over time.

In a further aspect of the invention, there is provided a catheter assembly comprising:
  a catheter having a reception space at a distal end of the catheter for receiving a collapsed medical device therein; and
  means for applying pressure to a wall of the catheter around the reception space and/or to a collapsed medical device received in the reception space to distribute loading stresses in the catheter wall and/or the collapsed medical device.

BRIEF DESCRIPTION OF THE DRAWINGS

The invention will be more clearly understood from the following description of some embodiments thereof, given by way of example only, with reference to the accompanying drawings, in which:

FIG. 1 is a side, partially cross sectional view of an embolic protection filter;

FIGS. 2(a) to 2(c) are schematic views illustrating the coating of the filter with an adhesion preventing material;

FIGS. 7 to 16 are enlarged cross-sectional views illustrating the interaction of various adhesion prevention materials with hydrophilic coatings in various arrangements;

FIGS. 22 and 24 are cross-sectional, side views of a funnel according to the invention;

FIG. 23 is an enlarged cross-sectional, end view of a filter passing through the funnel of FIGS. 22 and 23;

FIG. 25 is an enlarged view along line XXV-XXV in FIG. 23;

FIG. 27 is a side, cross-sectional view of a catheter according to the invention;

FIG. 28 is a schematic representation of 1/porosity along a part of the catheter of FIG. 27;

FIG. 29 is a side, cross-sectional view of another catheter according to the invention;

FIG. 30 is a schematic representation of 1/porosity along a part of the catheter of FIG. 29;

FIG. 31 is a side, cross-sectional view of a further catheter according to the invention;

FIG. 32 is a schematic representation of 1/porosity along a part of the catheter of FIG. 31;

FIGS. 33 and 35 to 38 are schematic views of a catheter according to the invention, in use;

FIGS. 34 and 39 to 40 are schematic views of another catheter according to the invention, in use;

DETAILED DESCRIPTION OF THE INVENTION

Figure 2D:
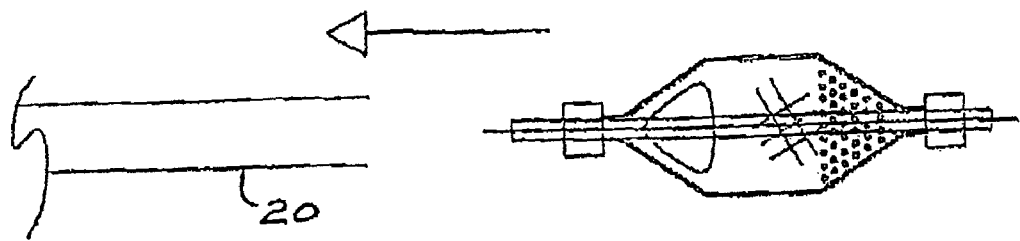
FIGS. 2(d) and 2(e) are schematic views illustrating the loading of the filter into a delivery catheter.

Referring to the drawings and initially to FIG. 1 thereof, there is illustrated an embolic protection filter 1 which in this case comprises a collapsible filter body 2 and a filter support 3 for the filter body 2. In the embodiment of FIG. 1, the filter body 2 is located externally of the filter support 3. The filter support 3 is mounted around an inner tube 8. The inner tube 8 has a guidewire lumen 12 therethrough, through which a guidewire may pass for exchange of the filter 1 over the guidewire.

The filter body 2 has an inlet end 4 and an outlet end 5. The inlet end 4 has one or more, and in this case two, large inlet openings 6 which are sized to allow blood and embolic material enter the filter body 2. The outlet end 5 has a plurality of small outlet openings 7 which are sized to allow through passage of blood but to retain undesired embolic material within the filter body 2. In this way, the filter 1 captures and safely retains any undesired embolic material in the blood stream within the filter body 2 while facilitating continued flow of blood through the vascular system. Emboli are thus prevented from flowing further downstream through the vascular system, which could otherwise have potentially catastrophic results.

Figure 2E:
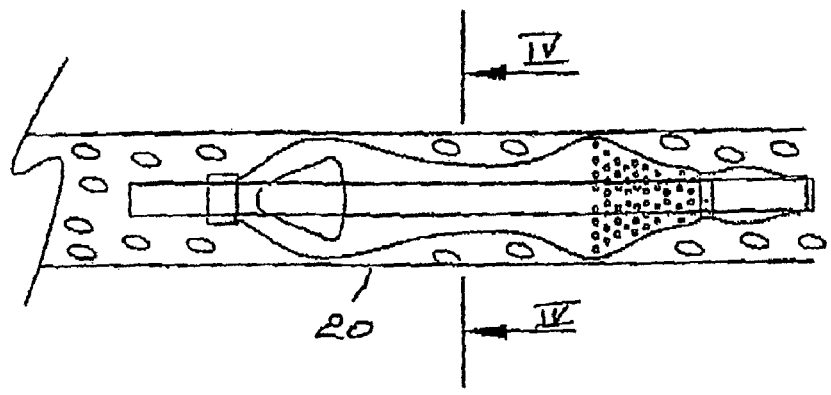

The filter 1 is movable between a low profile, collapsed configuration (FIG. 2(e)) for transport through a vasculature, and an expanded configuration (FIG. 1) for deployment in the vasculature. As particularly illustrated in FIG. 1, in this expanded configuration, the filter body 2 is supported in the expanded configuration by the filter support 3 so as to maximize the internal volume of the filter body 2 to capture and safely retain as much embolic material as possible.

The filter body 2 may be of an oriented polymeric material, as described in International Patent Application No. PCT/IE01/00087 (U.S. Ser. No. 09/887,893), the relevant contents of which are incorporated herein by reference The filter 1 may have a coating of a biocompatible material, in this case a hydrophilic material, around the external surface of the filter body 2 and around the internal surface of the filter body 2.

Fluid mechanics dictates that blood flowing through a pore or series of pores is subjected to shearing forces. Filtration devices are by their nature shearing devices. Excessive shearing forces can causes the activation of platelets which can cause the formation of thrombus. Activated platelets adhere to surfaces and attract more platelets to the site. Passing platelets stick to those already at the site and this leads to a cascade. Fibrin deposition is also a consequence and can form an insoluble threadlike mesh on the filter membrane. Fibrin formation on the filter is undesirable. It may have embolic potential if it enters the blood stream. It may also act to block filter pores reducing the blood flow through the filter and causing localized high shear zones in the remaining open holes.

Biocompatible coatings or surfaces are often used to prevent thrombus and fibrin formation on a filter. Biocompatible coatings with hydrophilic properties aid biocompatibility by providing a non-thrombogenic and non-stick surface.

The fluid membrane interactions resulting from the activation of the hydrophilic surface layer, which is liquid or substantially liquid, allows the device to resist fibrin build-up and minimize the risk of clots forming in the blood stream. The interactive surface layer, being of a liquid form could typically contain silicone, lipids, heparin or the like.

Figures 4, 5:
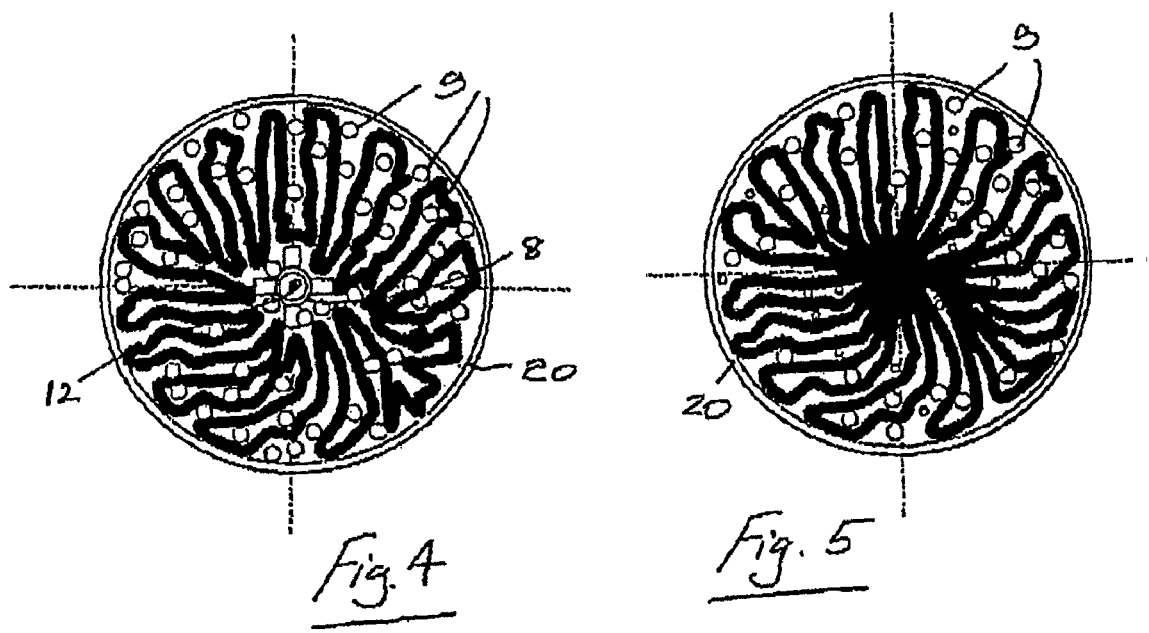
FIG. 4 is a cross sectional view of the filter in the collapsed loaded configuration of 2(e)
FIG. 5 is a cross sectional view of an alternative filter in the collapsed loaded configuration.

As illustrated in FIG. 4, when the filter 1 is in the collapsed configuration, the filter body 2 is tightly folded over upon itself. FIG. 5 illustrates a similar arrangement to FIG. 4 but with no longitudinal support/frame shown.

To prevent the relatively sticky hydrophilic coating on one fold of the filter body 2 adhering to an adjacent fold of the filter body 2, an adhesion preventing material 9, such as a silicon fluid, or a silicon gel, or an aqueous material, is applied to the external surface of the filter body 2 and to the internal surface of the filter body 2 prior to loading the filter 1 into a delivery catheter 20.

The adhesion preventing material 9 may be applied in any convenient manner such as by dipping the filter 1 into a bath 15 of the adhesion preventer 9 as illustrated in FIGS. 2(a) to 2(c).

As illustrated partially in FIGS. 4 and 5, the adhesion preventing material 9 provides a means of spacing adjacent folds of the filter body 2 apart. Any hydrophilic coating on one fold of the filter body 2 is thus prevented from adhering to an adjacent fold of the filter body 2, even when the filter body 2 is tightly wrapped down in the collapsed configuration.

The delivery catheter 20 may comprise an outer catheter shaft with an expansible pod at a distal end of the outer catheter shaft, and an inner catheter shaft extending through the outer catheter shaft. In the delivery configuration illustrated, the pod extends distally of the inner shaft to facilitate reception of the collapsed filter 1 within the pod. The inner shaft is movable distally relative to the outer shaft to deploy the filter 1 out of the pod.

The delivery catheter may be similar to that described in our International Patent Applications Nos. PCT/IE98/00093 (U.S. Ser. No. 09/188,472), PCT/IE01/00052 (U.S. Ser. No. 09/838,544) and PCT/IE01/00053 (U.S. Ser. No. 09/838,545), the relevant contents of which are incorporated herein by reference.

In use, when the adhesion preventing material 9 has been applied to the filter body 2 (FIG. 2(d)), the filter 1 is then collapsed and loaded into the delivery catheter 20 (FIG. 2(e)). A funnel may be used to assist collapse of the filter 1 during loading into the delivery catheter 20.

Figure 2F:
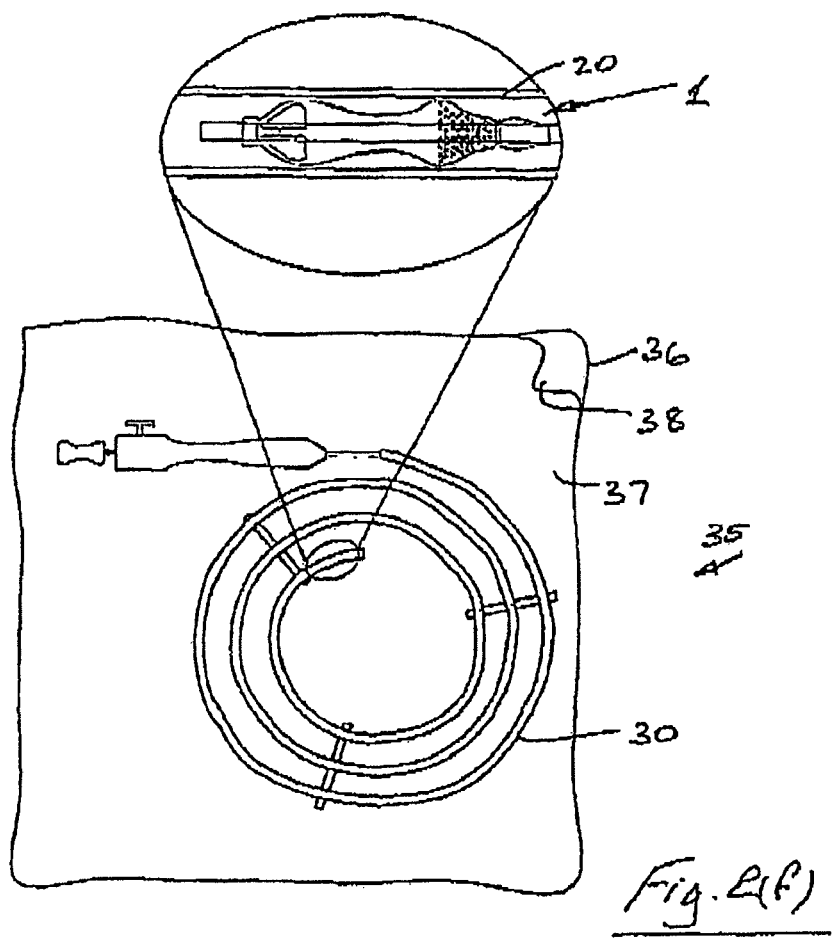
FIG. 2(f) is a schematic view of the filter loaded into a delivery catheter in a hoop mounted in a sterile pouch with an enlarged detail of a distal end of the delivery catheter with the filter in place.
Figure 2G:
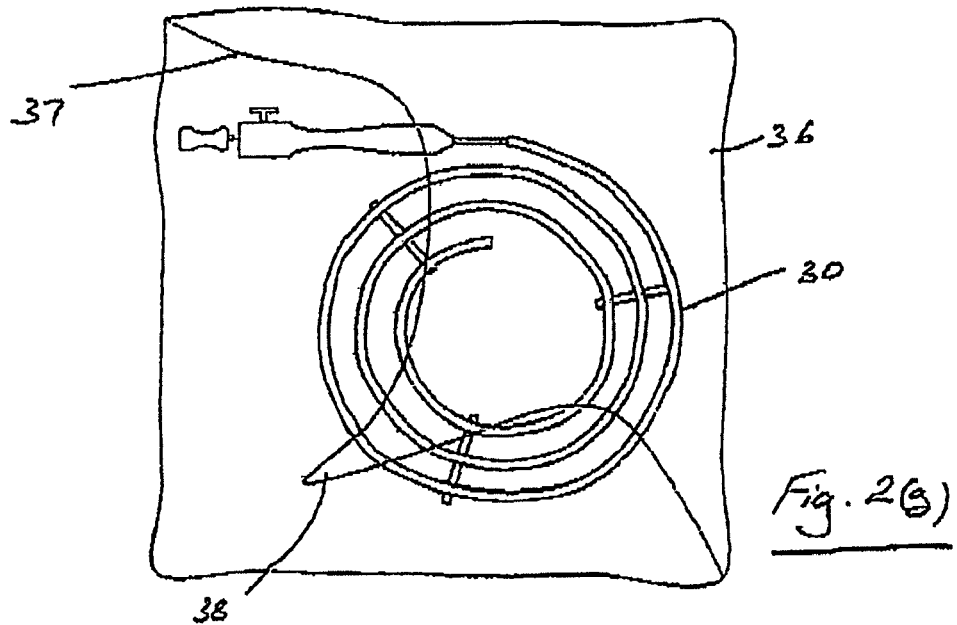
FIGS. 2(g) and 2(h) are schematic views illustrating the removal of the hoop from the pouch.
Figure 2H:
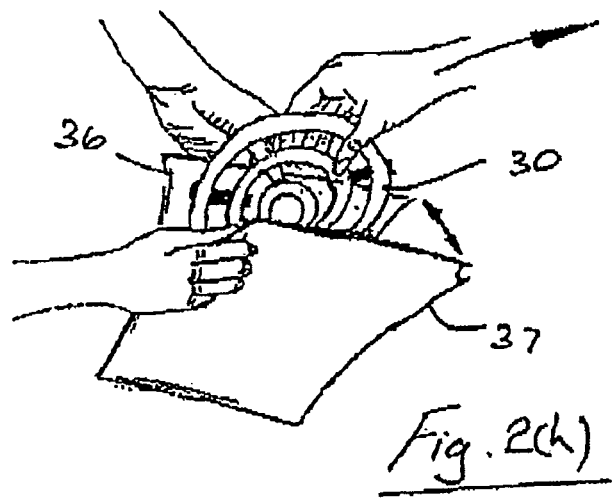
Figure 2I:
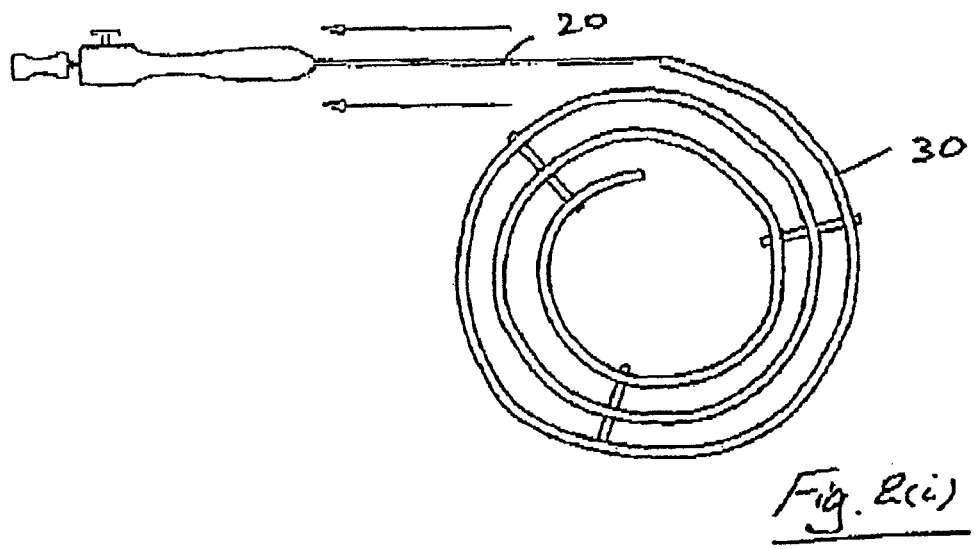
FIGS. 2(i) and 2(j) are schematic views illustrating the removal of the delivery catheter from the hoop.
Figure 2J:
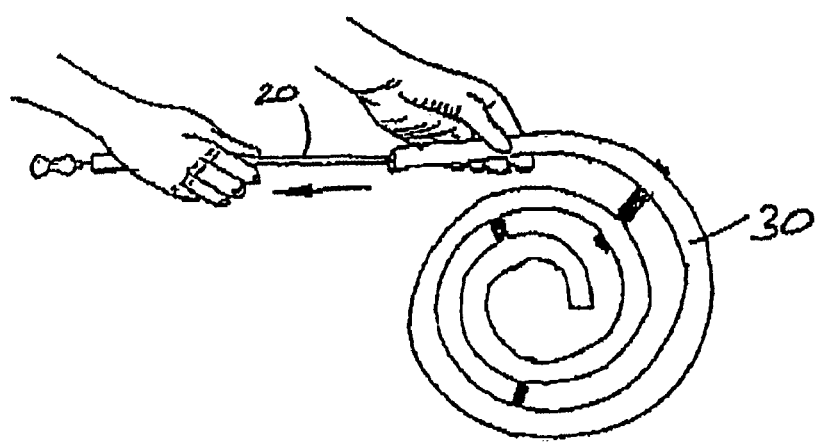
Figure 2K:
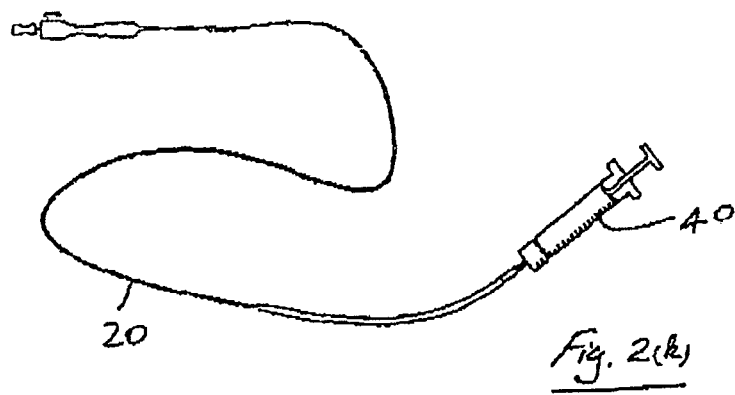
FIG. 2(k) is a schematic view illustrating the flushing of the delivery catheter.
Figure 2L:
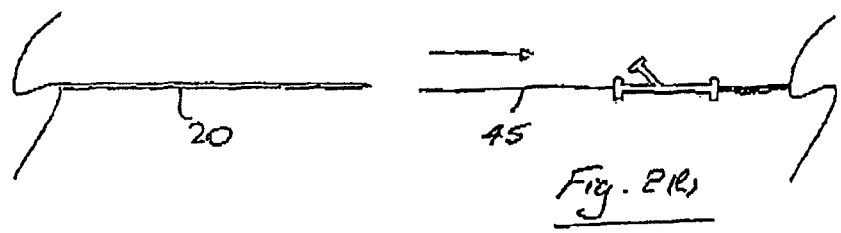
FIGS. 2(l) to 2(n) are schematic views illustrating the loading of the delivery catheter onto a pre-deployed guidewire.
Figure 2M:
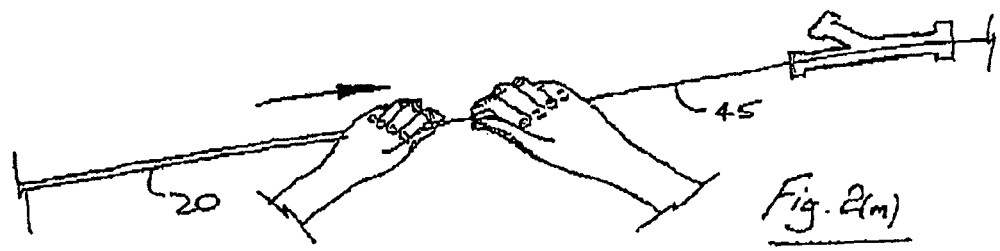
Figure 2N:
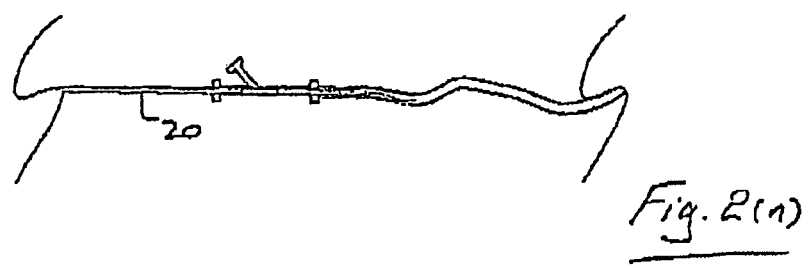
Figure 20:
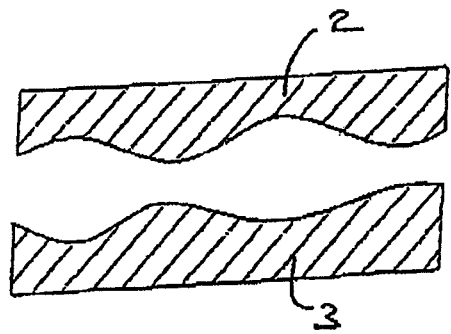
FIG. 20 is an enlarged view of portion of another filter.

The delivery catheter 20 with the filter 1 loaded in a collapsed configuration may be threaded through a hoop 30 which in turn is packaged aseptically in a sterile pouch 35 (FIG. 2(f)) having a backing sheet 36 and a cover sheet 37 with a pull tab 38 for opening the pouch as illustrated in FIG. 2(g). The hoop 30 containing the delivery catheter can then be removed as illustrated in FIG. 2(h). The delivery catheter 20 is removed from the hoop as illustrated in FIGS. 2(i) and 20). The removed delivery catheter 20 may then be flushed using a saline injector 40 (FIG. 2(k)). Alternatively or additionally the filter and delivery catheter may be pre-flushed prior to packaging.

Figure 3:
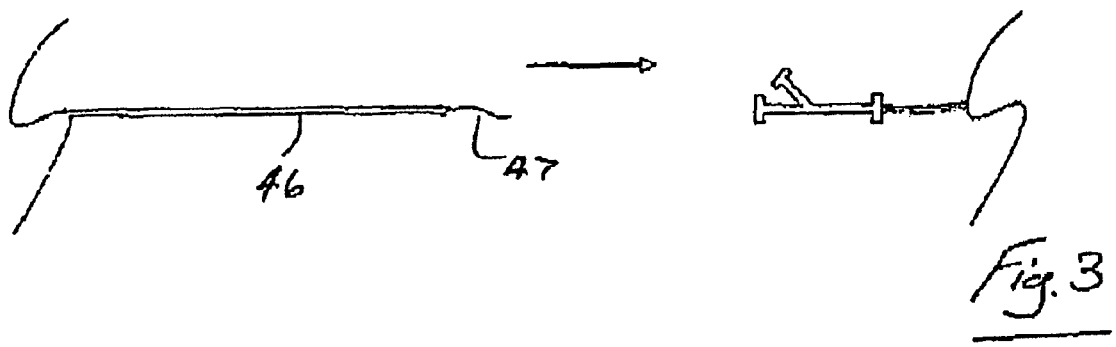
FIG. 3 is a schematic view illustrating the loading of a delivery catheter in an arrangement in which a guidewire extends through the delivery catheter prior to entry into the vasculature.

In the arrangements illustrated in FIGS. 2(e) to 2(n) the delivery catheter 20 with the filter at the distal end thereof may be threaded over the proximal end of a guidewire which has been deployed in the vasculature of a patient. Alternatively, as illustrated in FIG. 3 the delivery system may comprise a delivery catheter 46 with a guidewire 47 extending therethrough to which a filter is connected and the delivery system is led through the vasculature Via a guide catheter, sheath or catheter.

The loaded delivery catheter 20 is advanced through the vasculature to deliver the collapsed filter 1 to a desired site in the vasculature. The site of deployment of the filter 1 in the vasculature is typically downstream of a treatment site, such as a region of stenosis in the vasculature.

The filter 1 is deployed out of the delivery catheter 20 at the desired site in the vasculature. The filter support 3 expands radially outwardly to support the filter body 2 in tubular apposition with the interior wall of the vasculature. During the subsequent performance of a treatment procedure, on the vasculature the filter 1 captures and safely retains any embolic material in the blood stream within the filter body 2.

After completion of the treatment procedure, the filter 1 is collapsed down and retrieved into a retrieval catheter with any retained embolic material within the filter body 2. The retrieval catheter is then withdrawn from the vasculature with the filter 1 within the retrieval catheter.

The delivery, deployment and retrieval of the embolic protection filter of the invention, as described above, is similar to that described in our International Patent Applications Nos. PCT/IE98/00093 (U.S. Ser. No. 09/188,472), PCT/IE01/00052 (U.S. Ser. No. 09/838,544) and PCT/IE01/00053 (U.S. Ser. No. 09/838,545), the relevant contents of which are incorporated herein by reference. The filter 1 may be slidably exchanged over the guidewire without any attachment means between the filter 1 and the guidewire. A distal stop on the guidewire assists in retrieval of the filter 1. The guidewire may remain in the vasculature after retrieval of the filter 1.

Figure 6:
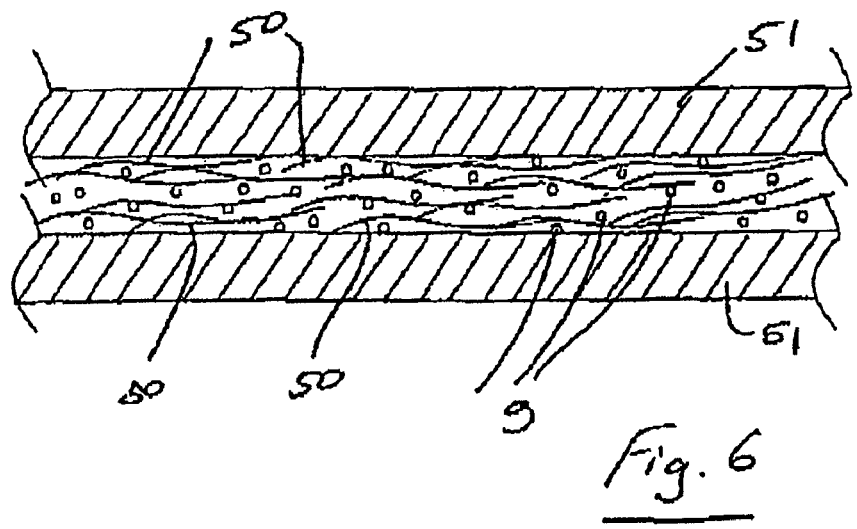
FIG. 6 is an enlarged cross sectional view showing the region between adjacent parts of the filter body in the collapsed configuration.

Referring now to FIG. 6, hydrophilic coating material 50 on adjacent parts of the filter membrane 51, when folded are illustrated by wavy lines. In the invention molecules of the adhesion prevention material 9 are interspersed between the coating 50, thus preventing the coating 50 from adjacent membranes interacting and becoming attached.

FIGS. 7 to 9 illustrate the interaction of the molecules of the hydrophilic coatings 50 of adjacent filter membrane layers when water is excluded or included. FIG. 8 describes two non-contacting hydrophilically coated surfaces. In the case where these two coatings are brought into intimate contact in the presence of water the hydrophilic chains become entangled and adhered as shown in FIG. 9. This may be the case with a wrapped down filter membrane (intimate pressurized contact) which sees moisture (sterilization or atmospheric exposure). This may hinder/prevent filter deployment from a sheath in the vasculature. FIG. 7 describes two hydrophilically activated (water present) surfaces which are in relatively close contact. Removing the activation reagent (water) from the hydrophilic surfaces and compressing results in the coated surfaces becoming stuck together.

FIGS. 10 and 11 illustrate the reversible activation/deactivation of the hydrophilic properties of the surface with the addition/removal of water. FIG. 10 shows the non-activated case. FIG. 11 shows an activated hydrophilic surface with a swollen and lubricious configuration.

Figure 12:
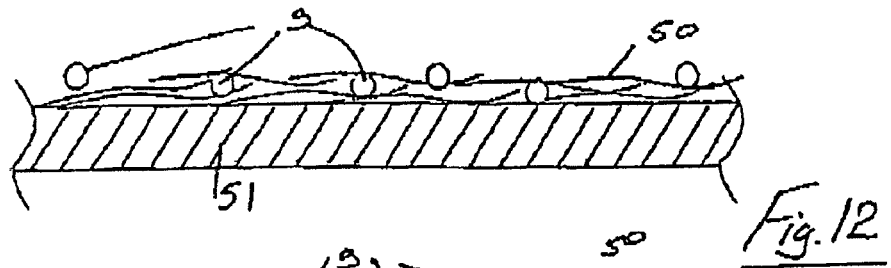

FIG. 12 schematically illustrates the use of an adhesion prevention material 9 of relatively large molecular weight such as a high viscosity silicone fluid with a viscosity in the region of 5,000 10,000 centipoise.

Figure 13:
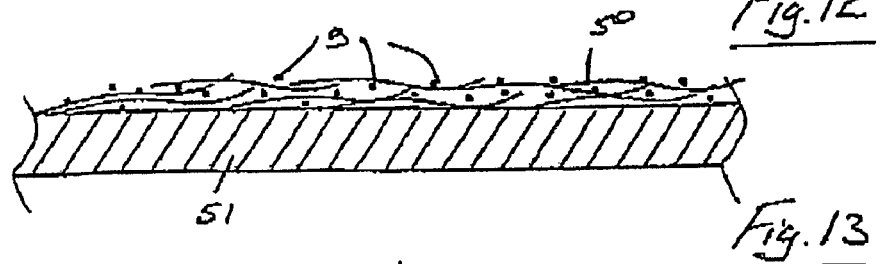

FIG. 13 schematically illustrates the use of an adhesion prevention material 9 of relatively low molecular weight such as a low viscosity silicone fluid with a viscosity in the region of 1-100 centipoise. In general, adhesion prevention materials can be processed in such a way as to tailor the required molecular weight.

Exemplary examples of adhesion preventers are silicone fluids, PDMS (poly dimethyl siloxane), PEO (polyethylene oxide), PEG (polyethylene glycol), PPO (polypropylene oxide), PPG (polypropylene glycol), lipophilic fluids, hydrophilic fluids, co-polymers of PDMS and PEO and/or PPO and surfactants. Examples of low molecular weight adhesion preventers are silicone fluids and aqueous solutions.

Figure 14:
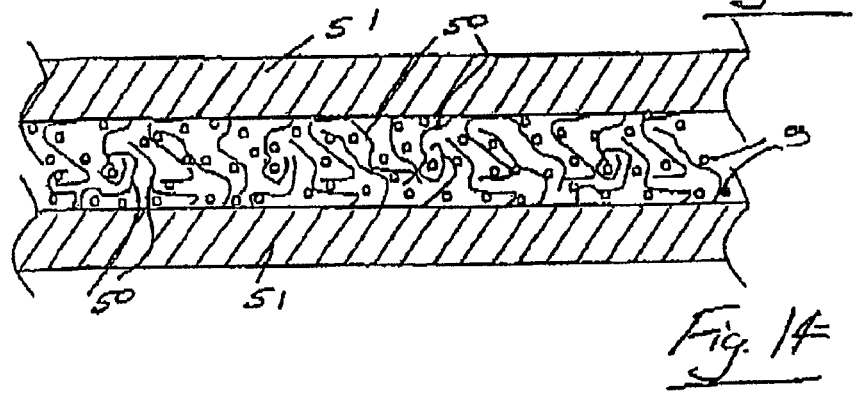

FIG. 14 illustrates the use of the adhesion prevention material 9 to prevent sticking of the hydrophilic coatings on adjacent filter membrane portions when folded into the collapsed configuration even when the hydrophilic is activated. This shows the case where the hydrophilically coated surfaces with adhesion preventer of FIG. 6 are in pressurized contact and have been activated with water. The adhesion preventer is dispersed between the activated hydrophilic chains and prevents the coatings sticking together even though they are in intimate contact. The adhesion preventer does not evaporate from the system and retains its ability to prevent the molecular interaction (such as van der Waal's forces) of neighbouring hydrophilic chains. The adhesion preventer acts to enable successful deployment of the pre-loaded filter in the vasculature.

Figure 15:
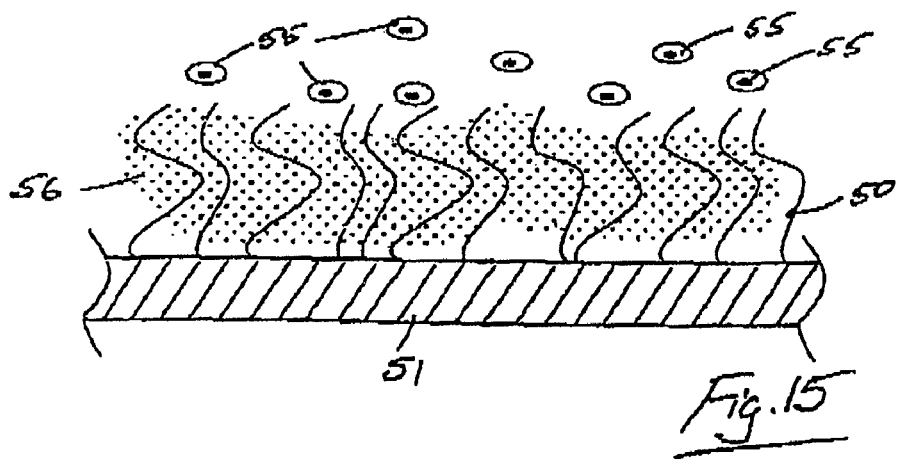
Figure 16:
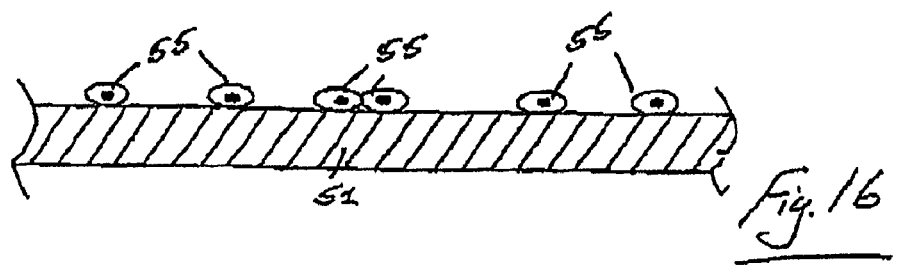

FIGS. 15 and 16 schematically illustrate the benefits of using a hydrophilic coating in blood contacting applications. Most thrombogenic coatings are also hydrophilic. FIG. 16 illustrates the base membrane 51 without a hydrophilic surface. When blood contacting, this non-hydrophilically coated membrane 51 is not a very passive surface. Cells and/or biological material 55 may adhere to the surface and cause a cascade of fibrin/clot build-up. FIG. 15 shows the membrane 51 with a hydrophilic coating activated with water 56. This is now extremely lubricious with a high water content. Due to this high water content hydrophilic cellular and biological material adhesion and cascade is minimized.

Figure 17:
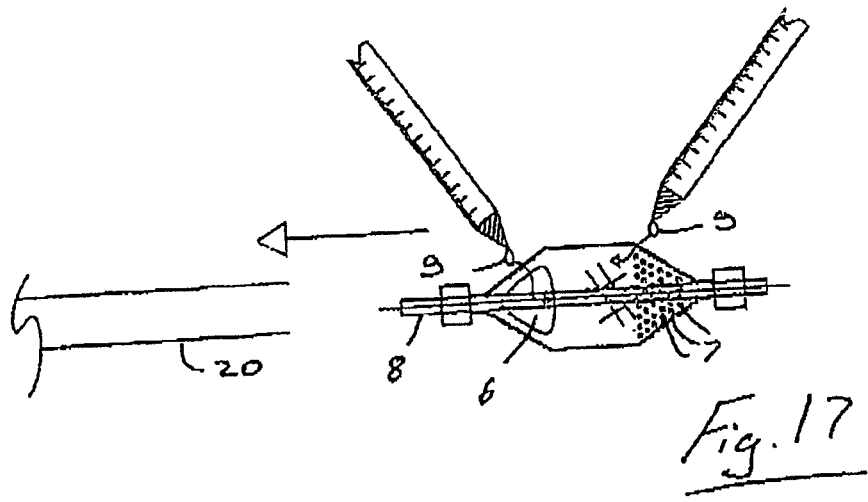
FIG. 17 is a schematic view illustrating an alternative method for coating a filter with an adhesion preventing material.

FIG. 17 illustrates another method of applying an adhesion prevention material 9 prior to loading into a delivery catheter.

Figure 18:
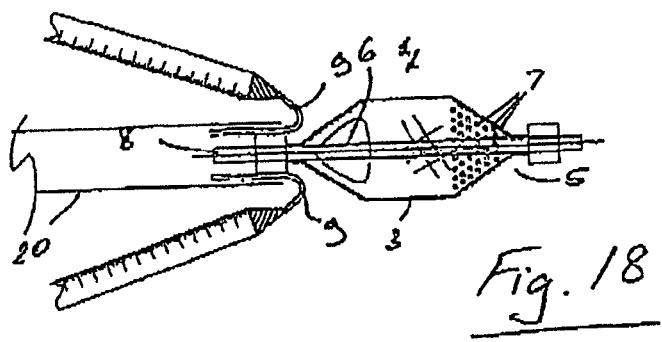
FIG. 18 is a schematic view illustrating an alternative method of loading a filter into a delivery catheter.

It will be appreciated that the adhesion preventing material 9 may be applied to the external surface of the filter body 2 and to the internal surface of the filter body 2 during collapse and loading of the filter 1 into the delivery catheter 20, as illustrated in FIG. 18.

Figure 19:
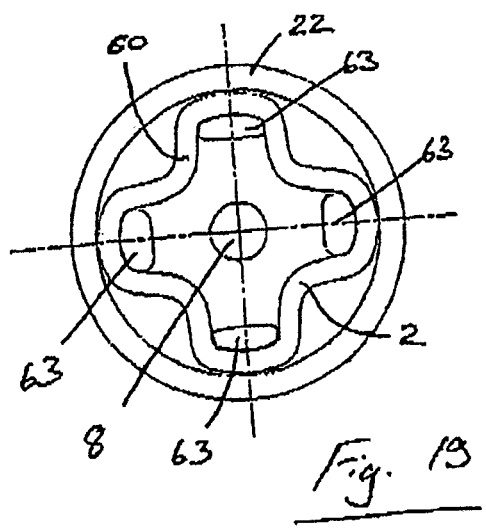
FIG. 19 is an end view of another embolic protection filter loaded into a catheter.

In FIG. 19, there is illustrated another embolic protection filter 60 according to the invention, which is similar to the filter 1 described above, and similar elements in FIG. 9 are assigned the same reference numerals. In this case, the filter support 3 comprises a plurality of arms 63 Are these shown which are configured to extend between adjacent folds of the filter body 2 as the filter 60 is collapsed down and loaded into the delivery catheter pod 22. Thus the filter support 3 provides the means of spacing adjacent folds of the filter body 2 apart, and so the hydrophilic coating on one fold of the filter body 2 is prevented from adhering to an adjacent fold of the filter body 2, even when the filter 60 is stored in a collapsed configuration within the pod 22 for a relatively long period of time.

The surface properties of the filter support 3 and/or the filter body 2 may be configured to minimize the possibility of adhering to one another. Furthermore, the surface formations on the filter support 3 and/or on the filter body 2 may be configured to minimize the possibility of adhering to one another, as illustrated in FIG. 20.

Figure 21:
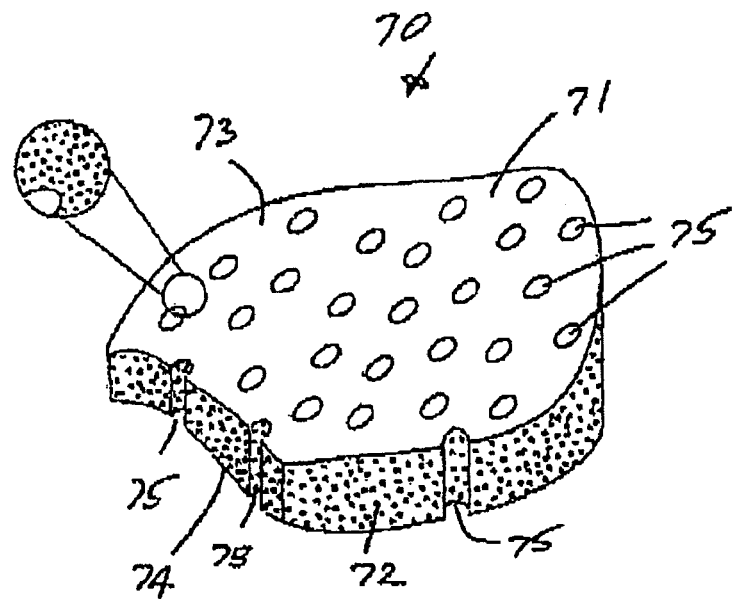
FIG. 21 is an enlarged perspective view of part of another filter according to the invention.

In FIG. 21, there is illustrated a further embolic protection filter 70 according to the invention, which is similar to the filter 1 described above. In this case, the filter body 71 comprises a storage space in the wall 72 of the filter body 71 for storing a biocompatible material, such as a hydrophilic material, in the wall 72 of the filter body 71 during transport through a vasculature. By storing the hydrophilic material in the wall 72 of the filter body 71 away from the external surface 73 of the filter body 2 and the internal surface 74 of the filter body 2, the filter 70 may be collapsed down without the risk of one fold of the filter body 2 adhering to an adjacent fold of the filter body 2. The filter 70 can thus be collapsed down and loaded into a delivery catheter for a relatively long period of time while ensuring that the filter 70 will expand fully radially outwardly when deployed in a vasculature.

The filter body 2 comprises a plurality of capillary channels 75 from the storage space in the wall 72 of the filter body 2 to the external surface 73 of the filter body 2 and to the internal surface 74 of the filter body 2. The channels 75 provide a means of delivering the hydrophilic material from the storage space in the wall 72 to the external and internal surfaces 73, 74 when the filter 70 is deployed in a vasculature.

Referring to FIGS. 22 to 25, there is illustrated a system according to the invention for loading a medical device, such as the embolic protection filter 1 described previously, into a catheter, such as the delivery catheter 20 described previously.

The system comprises a funnel 80 through which the filter 1 may be passed to collapse the filter 1 down to a wrapped configuration. Four inwardly protruding formations 81 are provided on the wall of the funnel 80. The protruding formations 81 extend longitudinally from an outlet end 82 of the funnel 80 in the form of four elongate fingers, and the formations 81 are equi-spaced around the circumference of the funnel 80.

The protruding formations 81 control the wrapping down of the filter 1 as the filter 1 is passed through the funnel 80 to collapse the filter 1.

In use, the funnel 80 is mounted to the distal end of the pod 22 of the delivery catheter 20 (FIG. 22). The filter 1 is then passed through the funnel 80 to collapse the filter 1 down to the wrapped configuration. As illustrated in FIG. 23, when the filter 1 enters the funnel 80 at the inlet end 83 of the funnel 80, the filter 1 is in the expanded configuration. When the filter 1 exits the funnel 80 at the outlet end 82, the filter 1 is collapsed down in the wrapped configuration, as illustrated in FIGS. 24 and 25.

In addition, as the filter 1 is passed through the funnel 80, the protruding formations 81 engage the filter body 2 and thereby control the wrap of the filter 1. By thus controlling the wrapping of the filter 1, a more uniform collapsed configuration may be achieved.

It will be appreciated that alternative means of collapsing the filter 1, and/or alternative means of controlling the wrap of the filter 1 may also be employed in addition to or as an alternative to the funnel 80.

Figure 26:
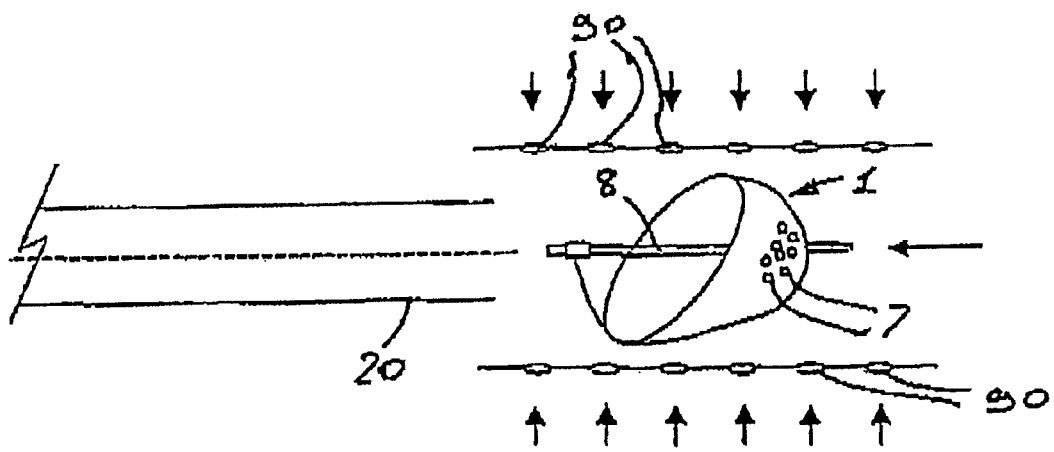
FIG. 26 is a schematic, side view illustrating loading of a medical device into a catheter.

For example one or more fluid jets 90 may be provided to direct a jet of fluid, such as air or a hydrophilic fluid, over the filter 1 to collapse the filter 1 down to the wrapped configuration, as illustrated in FIG. 26. By appropriately selecting the pressure of the fluid in each jet 90 the wrap of the filter 1 may also be controlled by the jet of fluid passing over the filter 1.

Referring to FIG. 27, there is illustrated a medical catheter 100 according to the invention. The catheter 100 comprises a catheter shaft 101 with an expandable pod 102 mounted to the distal end of the shaft 101. The pod 102 defines a reception space 104 suitable for receiving a collapsed medical device, such as an embolic protection filter, therein. In this manner, the catheter 100 may be configured for use as a delivery catheter to transport an embolic protection filter through a vasculature to a desired location in the vasculature downstream of a treatment site.

The wall of the pod 102 around the reception space 104 has a plurality of flushing openings 103 through the pod wall and evenly spaced along the pod 102. The provision of these flushing openings 103 in the pod wall enables the filter to be effectively flushed of all air bubbles, while the collapsed filter is positioned within the reception space 104, without the risk of the pressure of the flushing liquid disturbing or forcing the collapsed filter out of the reception space 104.

Thus the catheter of the invention enables a filter to be loaded into the pod, and then stored in this pre-loaded arrangement until required for use. When the filter and catheter are subsequently required for use, the clinician may then flush the pre-loaded filter within the pod to ensure all air bubbles are removed from the filter and the pod.

Therefore it is not necessary for the clinician to load the filter into the pod at the site of use. In this case the clinician simply flushes the filter and the pod, and then inserts the catheter into a vasculature.

The catheter of the invention also enables a filter to be loaded into the pod, completely flushed of air bubbles while in the pod at the site of loading, and then stored in this pre-loaded, pre-flushed arrangement until required for use. In this case, it is not necessary for a clinician to load the filter into the pod, or to flush the filter at all before introducing the catheter into a vasculature.

It will be appreciated that by appropriately selecting the size, and/or the layout, and/or the concentration of the flushing openings 103 along the pod 102, the pressure of the flushing liquid on the collapsed filter in the pod 102 may be controlled.

For example, in the catheter 106 of FIG. 29, the concentration of the flushing openings 103 increases distally along the pod 102. This layout of flushing openings 103 results in 1/porosity decreasing distally along the pod 102, as illustrated in FIG. 30. The concentration of the flushing openings 103 may alternatively increase proximally along the pod 102. As a further alternative, in the catheter 107 of FIG. 31 the concentration of the flushing openings 103 increases from a centre of the pod 102 towards the proximal and distal ends of the pod 102. This layout of flushing openings 103 results in 1/porosity peaking at the centre of the pod 102 and falling off towards the proximal and distal ends of the pod 102, as illustrated in FIG. 32.

In FIG. 33, there is illustrated another medical catheter 110 according to the invention, which is similar to the catheter 100 of FIG. 27, and similar elements in FIG. 33 are assigned the same reference numerals.

In this case, the catheter 110 comprises three perfusion openings 111 in the wall of the pod 102 at the proximal end of the pod 102 (FIG. 33). It will be understood that any suitable number of perfusion openings may be provided in the catheter 110. FIG. 34 description. Replace existing FIG. 34 with FIG. 20 from page 35/59 sent Jan. 5, 2003.

Referring to FIGS. 35 and 35*a*, in use, a medical device such as the embolic protection filter 1 described previously may be collapsed down and positioned within the reception space 104 at the site of loading. When it is subsequently desired to use the catheter 110 and the collapsed filter 1, a sealing package around the catheter 110, which is held within a holding tube 113, is opened as described above. At the site of use, a flushing liquid may be introduced into the reception space 104 at the distal end of the pod 102, and the catheter 110 and the collapsed filter 1 are flushed proximally, for example by using a syringe 112 while the catheter 110 remains within a holding tube 113, as illustrated in FIGS. 35 and 35a.

When the flushing liquid is flushed through the reception space 104 and the collapsed filter 1, some of the flushing liquid will perfuse out through the openings 111 at the proximal end of the pod 102. Once the clinician sees the flushing liquid perfuse out through the openings 111, the clinician can be satisfied that the collapsed filter 1 has been fully flushed of any air bubbles and the flushing step may be terminated.

In this manner, the perfusion openings 111 provide a means of indicating the extent to which the reception space 104 and the collapsed filter 1 have been flushed. By monitoring this extent, the clinician will know when the collapsed filter 1 has been safely flushed of all air bubbles.

When the flushing step has been terminated, the syringe 112 is removed from the catheter 110. The catheter 110 may then be quickly and easily removed from the catheter holding tube 113.

In some cases the catheter 110 may be threaded over a guidewire 280, and advanced over the guidewire 280 through a vasculature to a desired site in the vasculature, such as downstream of a stenosed region of the vasculature.

Figure 36:
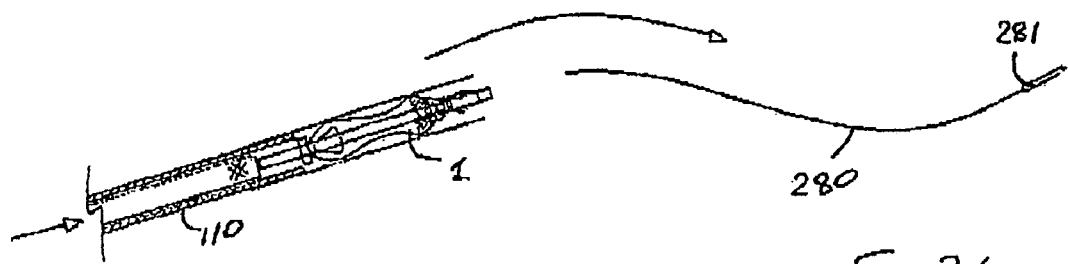

In the case of the guidewire 280 of FIG. 36, the guidewire 280 has a distal stop 281 at the distal end of the guidewire 280.

Figure 37:
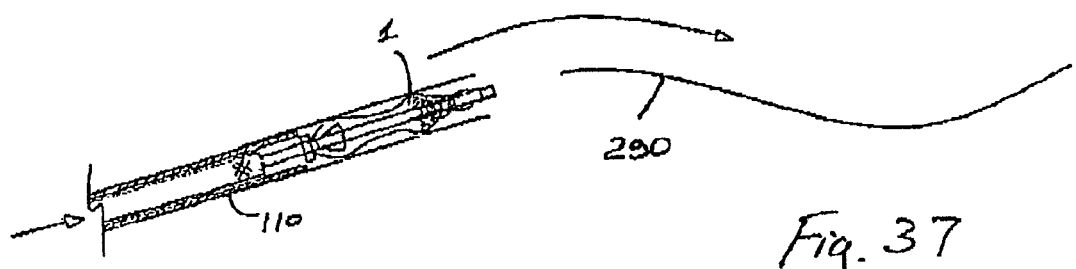

However the catheter 110 may also be advanced over a standard medical guidewire 290 without any stop formation at the distal end of the guidewire 290, as illustrated in FIG. 37.

Figure 38:
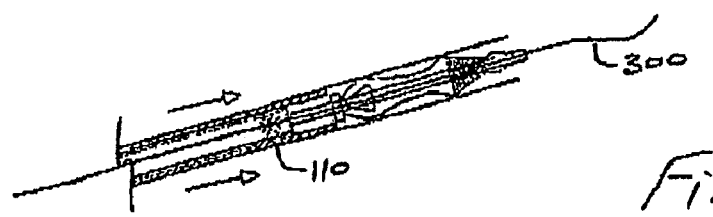

As a further alternative, the catheter may be advanced through the vasculature at the same time as the guidewire 300 is advanced through the vasculature, as illustrated in FIG. 38. This may arise in the circumstance in which the filter is constrained relative to the guidewire 300.

It will be appreciated that the flushing liquid may alternatively be introduced into the catheter 110 at the proximal end of the shaft 101, so that the catheter 110 and the collapsed filter 1 are flushed distally.

Figure 39:
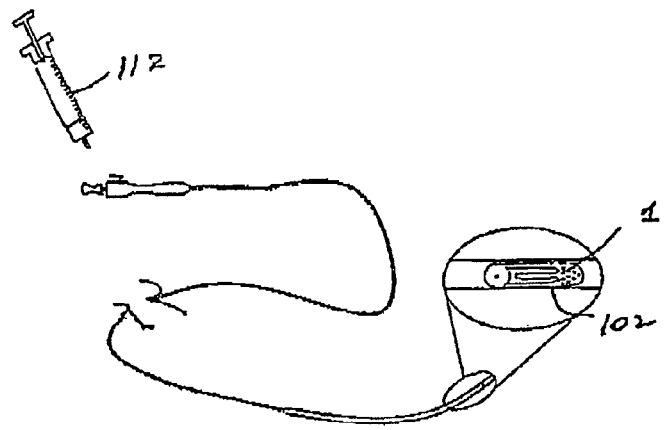

As illustrated in FIG. 34, a seal 116 may be releasably mounted at the distal end of the pod 102 after positioning the collapsed filter 1 in the reception space 104. The catheter 110 and the collapsed filter 1 are then flushed distally using the syringe 112, as illustrated in FIG. 39. When the flushing liquid has fully flushed the collapsed filter 1, the liquid engages against the seal 116 which reverses the flow of the flushing liquid. Some of the flushing liquid then flows proximally to the proximal end of the pod 102, where the flushing liquid perfuses out through the openings 111.

On initial distal flow of the flushing liquid, it is easiest for the flushing liquid to pass through the filter. The flushing liquid follows the path of least resistance which can be directed by altering the number and size of the openings 111. As pressure then builds up the flushing liquid exits through the openings 111.

When the clinician sees the flushing liquid perfuse out through the openings 111, the flushing step is terminated. The catheter 110 may then be quickly and easily removed from the catheter holding tube 113 for introduction into a vasculature of a patient.

Figure 40:
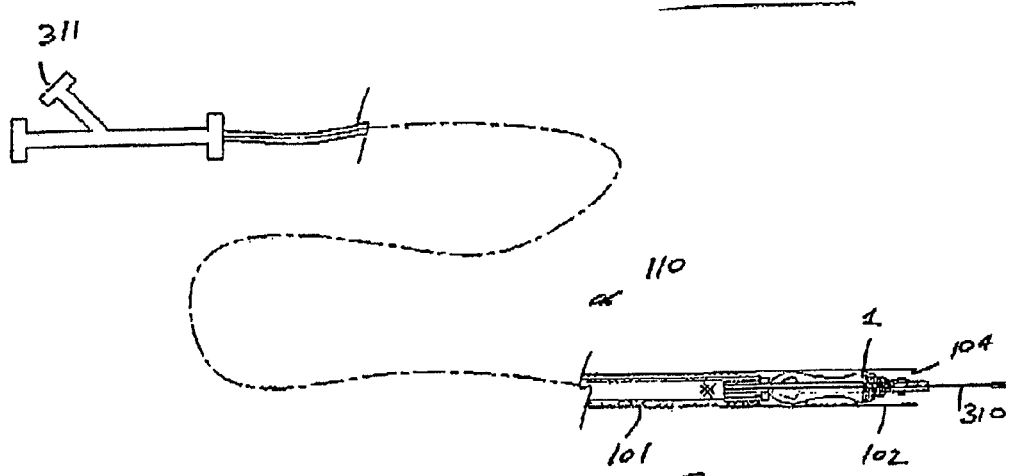

It will further be appreciated that the catheter 110 may be removed from the holding tube 113 before flushing the collapsed filter 1 and the reception space 104 (FIG. 39). The collapsed filter 1 and the reception space 104 may alternatively be flushed with a flushing liquid 311 at the site of loading (FIG. 40) before the catheter 110 is sealed within the package. When it is subsequently desired to use the catheter 110, the clinician simply needs to remove the holding tube 113 from the package, and remove the catheter 110 from the tube 113. The catheter 110 is then ready for introduction into a vasculature. In particular it is not necessary for the clinician to flush the catheter 110 at the site of use.

A sealing member 310 may be inserted into the filter 1 from the distal end of the filter during the flushing step.

The means to indicate the extent of flushing of the reception space of the pod and the collapsed filter 1 could alternatively be provided by a component separate from the catheter.

Figure 41:
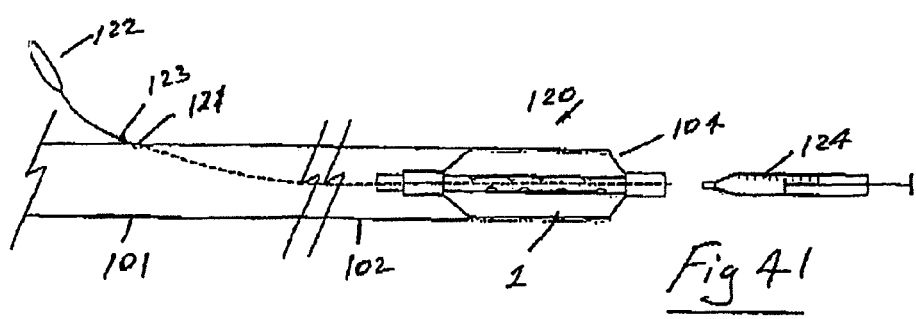
FIGS. 41 and 42 are side, cross-sectional views of further catheters according to the invention, in use.

For example, in FIG. 41 there is illustrated another catheter 120 according to the invention, which is similar to the catheter 110 of FIG. 33, and similar elements in FIG. 41 are assigned the same reference numerals.

The catheter 120 comprises an exit port 121 at the proximal end of the pod 102. A stylet 122 is extended through the reception space 104 and threaded through the collapsed filter 1 to exit the reception space 104 through the exit port 121 (FIG. 41).

The stylet 122 comprises an element 123 which is configured to change color upon contact with the flushing liquid. A suitable material for the color change element 123 is litmus.

By monitoring the color of the element 123, the clinician will be alerted when the collapsed filter 1 has been fully flushed of air bubbles.

In FIG. 41, the catheter 120 and the collapsed filter 1 are flushed proximally by introducing the flushing liquid into the reception space 104 at the distal end of the pod 102 using the syringe 124.

Figure 42:
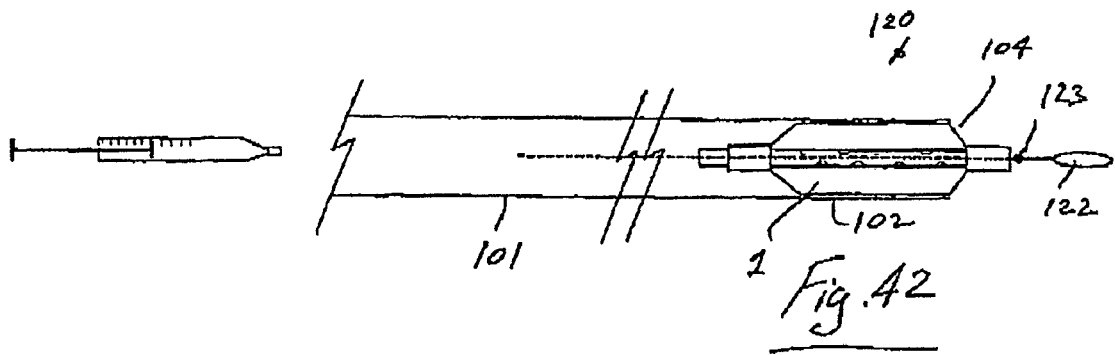

The catheter 120 and the collapsed filter 1 could alternatively be flushed distally by introducing the flushing liquid into the catheter 120 at the proximal end of the shaft 100 using the syringe 124, as illustrated in FIG. 42. In this case the stylet 122 is reversed so that the color change element 123 is downstream of the collapsed filter 1. In this way, by monitoring the color of the element 123, the clinician will be alerted when the collapsed filter 1 has been fully flushed of air bubbles.

Figure 43:
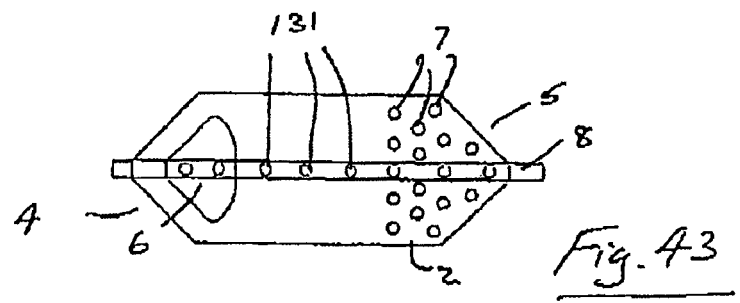
FIGS. 43 to 45 are side, partially cross-sectional views of medical devices according to the invention.

Referring to FIG. 43, there is illustrated another embolic protection filter 130 according to the invention, which is similar to the filter 1, and similar elements are assigned the same reference numbers.

In this case, the inner tube 8 of the filter 130 has a series of flushing openings 131 spread longitudinally along the inner tube 8 (FIG. 43). These openings 131 assist in the flushing of air bubbles from the filter 130 when the collapsed filter 130 is positioned in the reception space 104 of a catheter, by distributing the flushing liquid throughout the collapsed filter 130. Furthermore, the filter 130 may be flushed by introducing the flushing liquid into the guidewire lumen 12 of the inner tube 8. The flushing liquid then flows out of the guidewire lumen 12 thorough the flushing openings 131 to flush all air bubbles from the collapsed filter 130.

Figure 44:
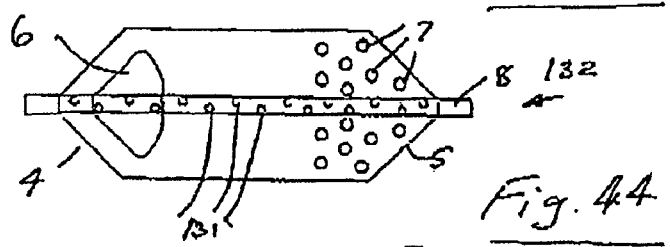

As illustrated in the filter 132 of FIG. 44, the distribution of the flushing openings 131 along the inner tube 8 may be selectively altered to achieve a thorough flushing of all air bubbles from the collapsed filter 132.

Figure 45:
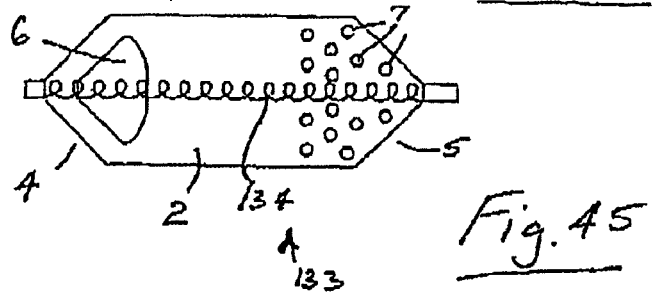

In the filter 133 of FIG. 45, the inner tube is provided in the form of a coiled spring 134. The spacings between the coils of the spring 134 provide flow pathways for the flushing liquid to pass out of the guidewire lumen 12 to achieve a thorough flushing of all air bubbles from the collapsed filter 133.

Figure 46:
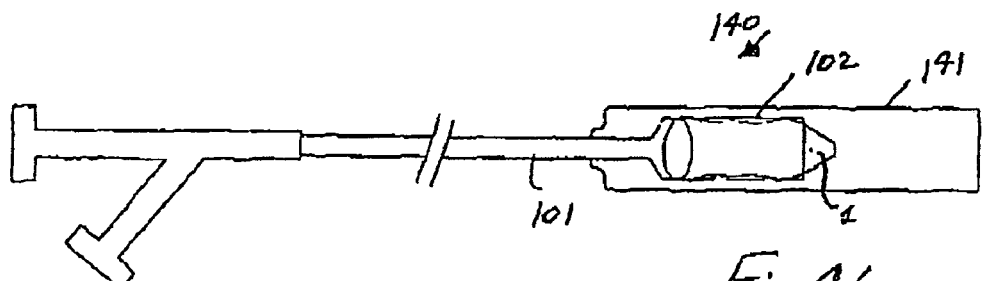
FIG. 46 is a schematic view of a loaded catheter according to the invention.
Figure 47:
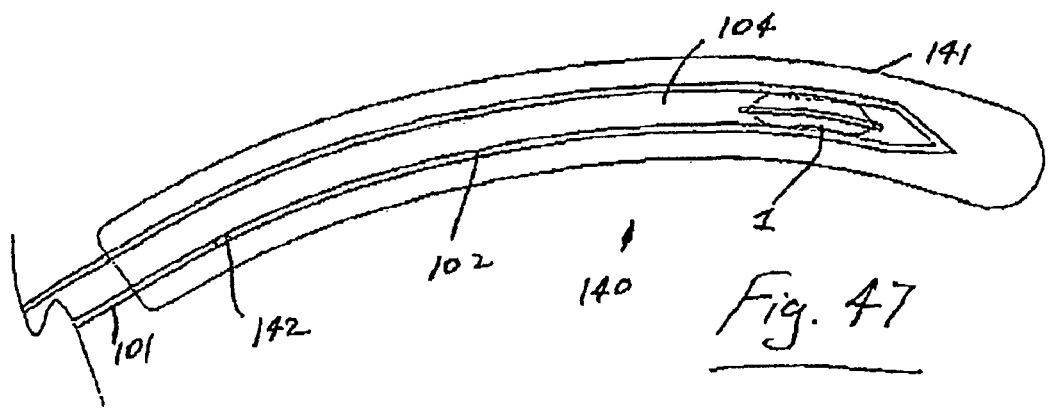
FIG. 47 is an enlarged, schematic view of the loaded catheter of FIG. 46.

FIGS. 46 and 47 illustrate a further catheter 140 according to the invention, which is similar to the catheter 120 of FIGS.

41 and 42, and similar elements in FIGS. 41 and 42 are assigned the same reference numbers.

The catheter 140 comprises an inlet port 142 at the proximal end of the pod 102 through which a flushing liquid may be introduced for flushing the reception space 104 and the collapsed filter 1.

The catheter 140 has a seal 141 for sealing around the reception space 104 with the collapsed filter 1 and some of the flushing liquid sealed within the seal 141.

In use, the filter 1 is collapsed down and positioned within the reception space 104. A source of flushing liquid 143 is then connected in communication with the inlet port 142, and a vacuum is drawn on the loaded filter 1 to create a pressure differential across the collapsed filter 1. This vacuum causes the flushing liquid to be drawn through the reception space 104 of the pod 102 and the collapsed filter 1 to dispel all air bubbles from the reception space 104 and the filter 1.

The seal 141 is then applied around the pod 102 with the collapsed filter 1 and some of the flushing liquid sealed within the seal 141 (FIG. 46). The seal 141, in this case, extends proximally over the inlet part 142 (FIG. 47).

The sealed catheter 140 may be stored in this arrangement for potentially long periods of time without the risk of any air bubbles entering the reception space 104 or the collapsed filter 1. When the catheter 140 is required for use, the seal 141 is broken. The catheter 140 may then be immediately used to transport the filter 1 through a vasculature without requiring the clinician to flush the reception space 104 or the filter 1 before use.

It will be appreciated that the catheter 140 may be configured for use as a rapid exchange catheter, in which case the flushing inlet port 142 may be used as a guidewire rapid exchange port.

Figure 48:
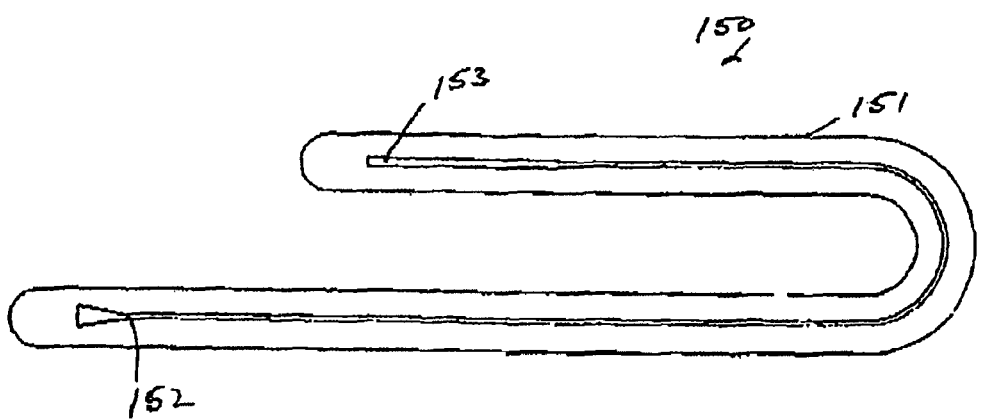
FIG. 48 is a plan view of another loaded catheter according to the invention.

FIG. 48 illustrates another catheter 150 according to the invention, which is similar to the catheter 140 of FIGS. 41 and 42.

The catheter 150 is an over-the-wire catheter, and the seal 151 extends along the full length of the catheter 150 from the proximal end 152 to the pod 153.

Figure 49:
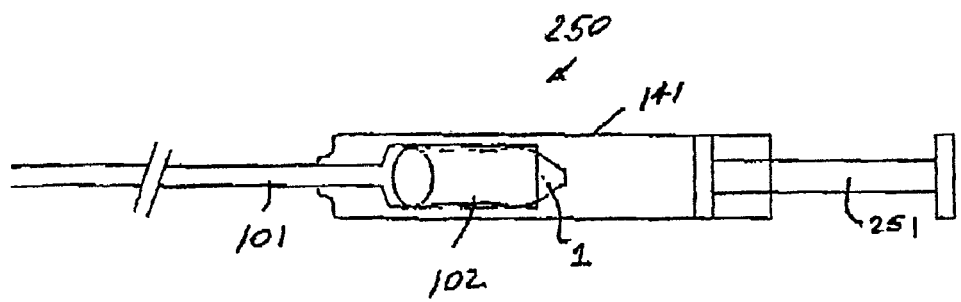
FIG. 49 is a schematic view of a further loaded catheter according to the invention.

FIG. 49 illustrates a further catheter 250 according to the invention, which is similar to the catheter 140 of FIGS. 41 and 42, and similar elements in FIG. 44 are assigned the same reference numerals.

The catheter 250 comprises a plunger 251 at the distal end of the seal 141.

When the clinician is ready to use the catheter 250, the plunger 251 may be moved proximally through the seal 141 to perform an additional flushing step at the site of use. Continued movement of the plunger proximally increases the pressure within the seal 141 eventually causing the seal 141 to burst. Thus the plunger 251 provides a simple, yet effective means of flushing the collapsed filter 1 and the pod 102 at the site of use, and of bursting open the seal 141.

Figure 50:
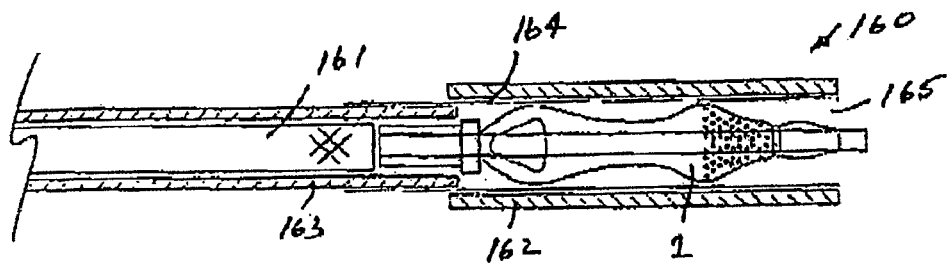
FIG. 50 is a partially cross-sectional, side view of a catheter assembly according to the invention.

In FIG. 50, there is illustrated a catheter assembly 160 according to the invention. The assembly 160 comprises a catheter 161 and a clamp sleeve 162.

The catheter 161 comprises a catheter shaft 163 with an expansible pod 164 at a distal end of the shaft 163. The pod 164 defines a reception space 165 for receiving a collapsed medical device, such as the embolic protection filter described previously.

The clamp sleeve 162 is releasably mounted to the catheter 161 positioned around the pod 164. The sleeve 162 reinforces the pod wall against radial creep when the collapsed filter 1 is loaded within the reception space 165.

In use, the filter 1 is collapsed down and positioned within the reception space 165. The clamp sleeve 162 is then positioned around the pod 164 to reinforce the pod wall against radial creep. In this way the filter 1 may be stored for a relatively long period of time in the collapsed configuration loaded into the catheter without creep of the filter and/or of the pod occurring.

When the catheter 161 is required for use, the clamp sleeve 162 is demounted from the catheter 161, and the catheter 161 is introduced into a vasculature to transport the filter 1 to the desired site in the vasculature.

Figure 51:
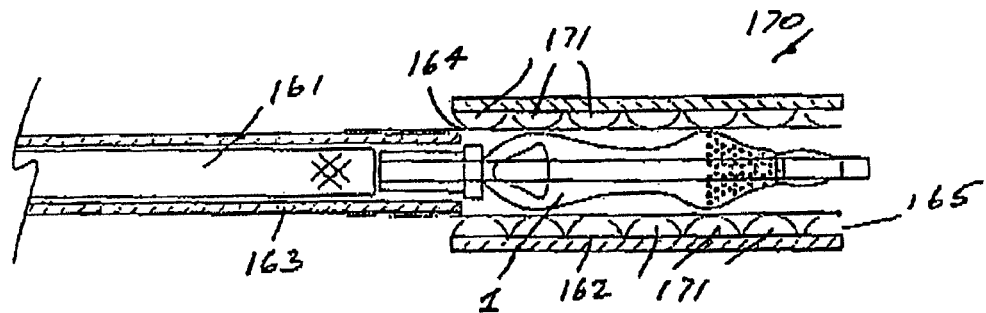
FIG. 51 is a partially cross-sectional, side view of another catheter assembly according to the invention.

FIG. 51 illustrates another catheter assembly 170 according to the invention, which is similar to the catheter assembly 160 of FIG. 45, and similar elements in FIG. 46 are assigned the same reference numerals.

In this case the clamp sleeve 162 comprises a plurality of inwardly protruding formations 171. The formations 171 engage the pod 164 to provide non-uniform reinforcement against radial creep to the pod 164 along the length of the pod 164.

Figure 52:
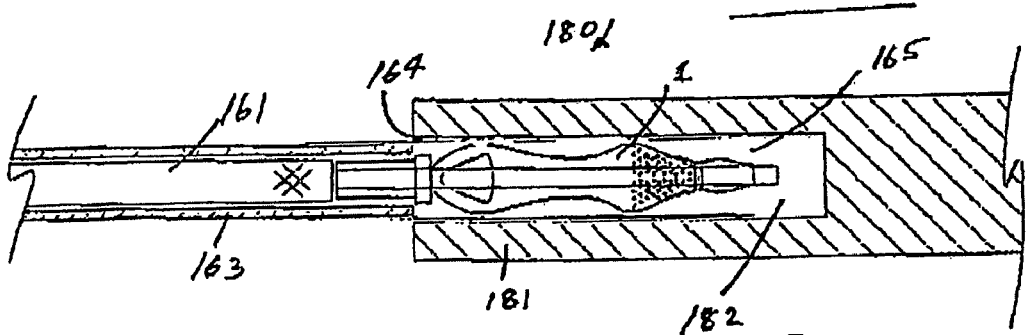
FIG. 52 is a partially cross-sectional, side view of a further catheter assembly according to the invention on a tray.

In the case of the catheter assembly 180 of FIG. 52, the clamp 181 is provided by a tray 181 for the catheter 161. The tray 181 has a recess 182 suitably configured to receive the catheter pod 164 when the collapsed filter 1 has been loaded into the reception space 165. The walls of the tray 181 around the recess 182 then engage against the pod 164 to reinforce against radial creep the pod 164 and the collapsed filter 1.

Figure 53:
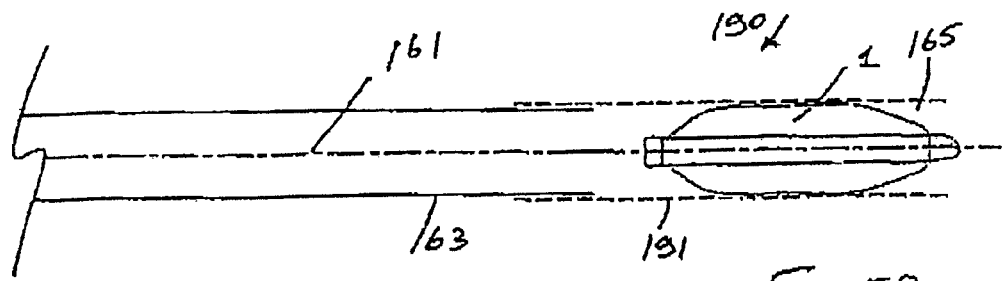
FIG. 53 is a partially cross-sectional, side view of another catheter assembly according to the invention.

Referring next to FIG. 53, there is illustrated another catheter assembly 190 according to the invention, which is similar to the assembly 160 of FIG. 50, and similar elements in FIG. 53 are assigned the same reference numerals.

The pod 191 of the catheter 190 has one or more reinforcing elements in the wall of the pod 191. There elements enhance the radial strength of the pod 191 and provide a means of reinforcing the pod wall against radial creep.

In another case, the pod may be at least partially of a composite construction for reinforcement against creep.

Figure 54:
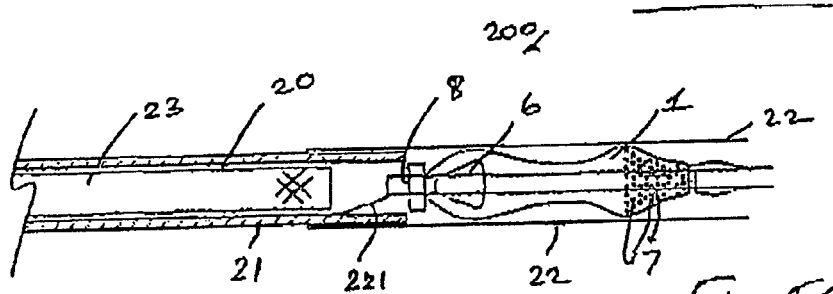
FIGS. 54 and 56 are side views of another catheter assembly according to the invention in use.
Figure 56:
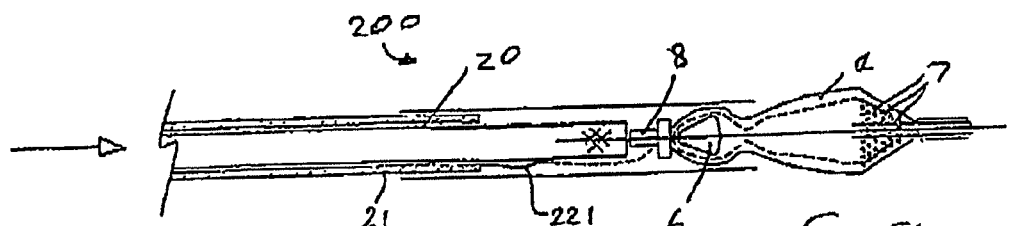

In the catheter assembly 200 of FIGS. 54 and 56, the assembly 200 comprises a tensioning wire 221 releasably attached to the inner tube 8 of the filter 1.

The wire 221 provides a means of elongating the filter 1 to ensure the filter 1 remains fully collapsed when loaded into a catheter reception space (FIG. 54). In this manner, the tensioning wire 221 aids in resisting radial and longitudinal creep of the filter 1 even if the filter 1 is stored for a relatively long period of time loaded in the catheter.

The wire 221 also provides a means of accurately holding the filter 1 in position in the pod 22 during storage of the loaded catheter assembly 200 and during advancement of the catheter assembly 200 through a vasculature (FIG. 54).

The filter 1 is deployed out of the pod 22 by moving the inner shaft 23 distally relative to the outer shaft 21 (FIG. 56). This relative distal movement of the inner shaft 23 breaks the wire 221 to facilitate deployment of the filter 1 out of the pod 22.

Figure 55:
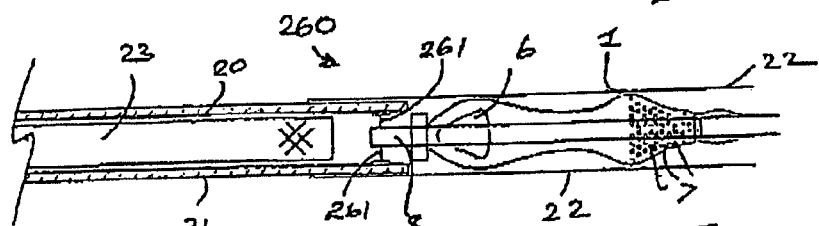
FIGS. 55 and 57 are side views of a further catheter assembly according to the invention in use.
Figure 57:
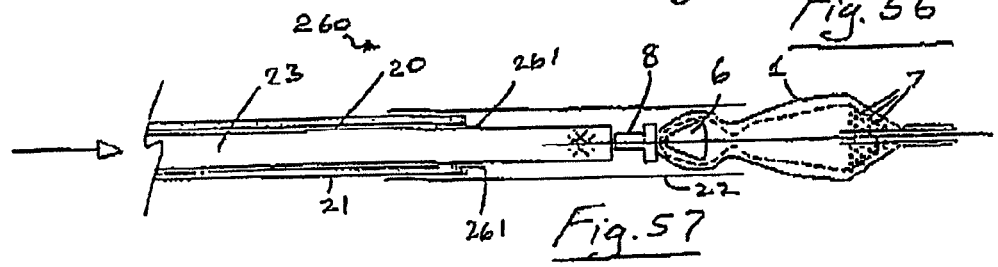
Figure 58:
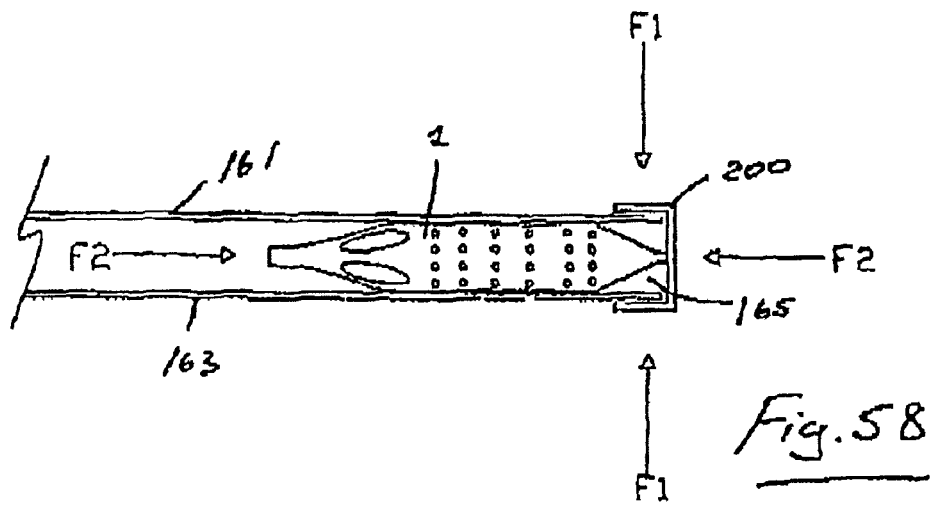
FIG. 58 is a partially cross-sectional, side view of another catheter assembly according to the invention.

The catheter assembly 260 of FIGS. 55 and 57 is similar to the catheter assembly 200 of FIGS. 56 and 58, and similar elements in FIGS. 55 and 57 are assigned the same reference numerals.

In this case, the assembly 260 comprises two "I"-shaped connectors 261 extending between the inner shaft 21 of the delivery catheter 20 and the inner tube 8 of the filter 1. The connectors 261 maintain the position of the filter 1 fixed within the pod 22 during storage of the loaded catheter assembly 260 and during advancement of the catheter assembly 260 through a vasculature (FIG. 55).

To deploy the filter out of the pod 22, the inner shaft 23 is moved distally relative to the outer shaft 21 (FIG. 57). This relative distal movement of the inner shaft 23 breaks the connectors 261 to facilitate deployment of the filter 1 out of the pod 22.

Such temporary tethering/connecting may be applied to other systems and the use is not restricted to a preloaded filter arrangement. They may be used in any suitable delivery system, especially those involving delivery over a bare guidewire.

Referring to FIG. 58, there is illustrated a further catheter assembly 210 according to the invention, which is similar to the assembly 160 of FIG. 50, and similar elements in FIG. 58 are assigned the same reference numerals.

The clamp 220, in this case, is in the form of an end-cap releasably mounted over the distal end of the pod 164.

When the filter 1 has been collapsed down and loaded into the reception space 165, pressure is applied to the pod 164 and/or to the collapsed filter 1. It has been found that by applying such pressures the loading stresses on the collapsed filter 1 and on the pod 164 are more evenly distributed.

The pressure may be applied in the radial direction F1 and/or in the longitudinal direction F2, and the magnitude of the applied pressure may be varied as desired. In addition, the pressure applied may remain constant over time, or may vary over time, for example in a cyclical manner.

Figure 59:
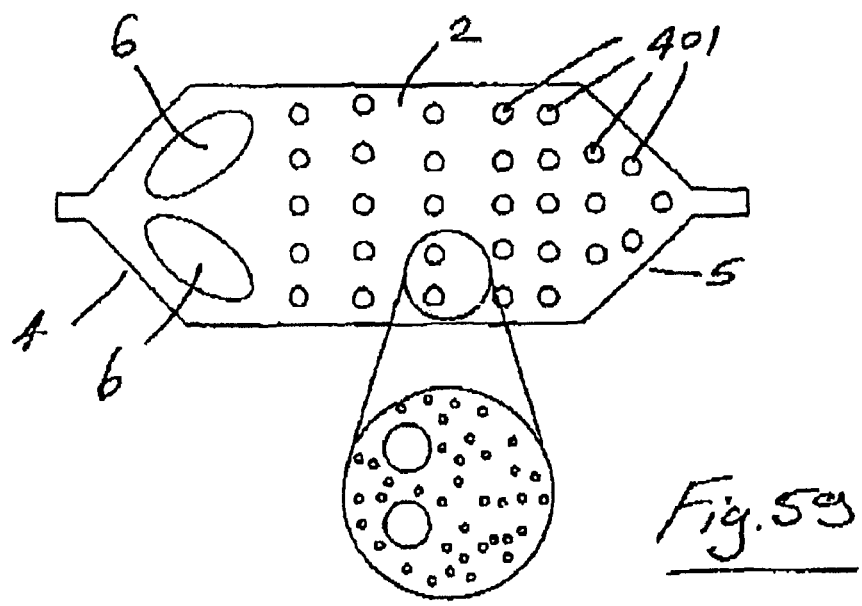
FIG. 59 is a side view of a medical device according to the invention.
Figure 60:
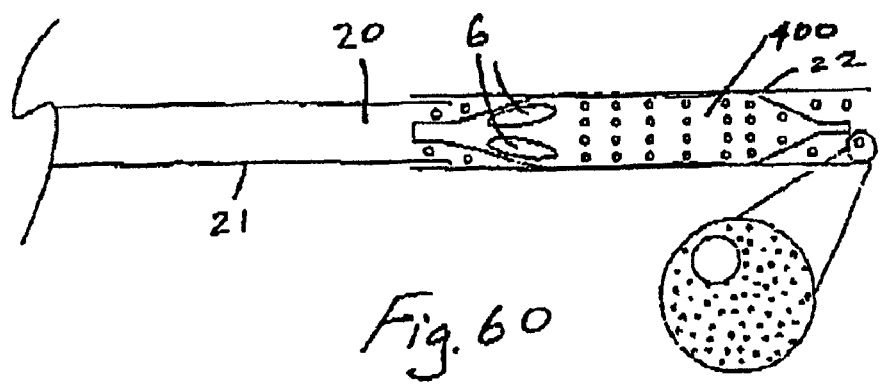
FIG. 60 is a cross-sectional, side view of the medical device of FIG. 59 loaded into a catheter.

Referring to FIGS. 59 and 60 there is illustrated a further embolic protection filter 400 according to the invention, which is similar to the filter 1 of FIG. 1, and similar elements in FIGS. 59 and 60 are assigned the same reference numerals.

In this case, the filter body 2 has a plurality of small outlet openings 401 at the outlet end 5 of the filter 400 and extending along the filter body 2 towards the inlet end 4, as illustrated in FIG. 59. In FIGS. 59 & 60 I think it is important to make reference to the liquid pores and the gas pores. Both the filter and pod may contain both liquid pores and gas pores. Gas pores provide some back pressure and ensure that no air pockets are generated. A gradient of hole sizes might be used to achieve the best flushing.

By providing outlet openings 401 along the central portion of the filter body 2, this configuration aids in minimising the possibility of the filter 400 creeping or the pod 22 creeping when the filter 400 is loaded within the pod 22 for periods of time, as illustrated in FIG. 60.

The invention is not limited to the embodiments hereinbefore described which may be varied in construction and/or detail.

What is claimed is:

1. An embolic protection system comprising:
   an embolic protection filter having a collapsed delivery configuration and an expanded deployed configuration, the embolic protection filter comprising a filter membrane and a coating for preventing self-adherence between folds of the filter membrane;
   a delivery catheter having a reception space, the embolic protection filter being housed in the collapsed configuration in the reception space of the delivery catheter; and
   a sealed sterile pouch housing the delivery catheter containing the filter in the collapsed configuration.

2. The embolic protection system as claimed in claim 1, wherein the embolic protection filter further comprises:
   a coating of biocompatible material for reducing fibrin build-up provided between the filter membrane and the coating for preventing self-adherence between folds of the filter membrane.

3. The embolic protection system as claimed in claim 1, wherein the coating for preventing self-adherence between folds of the filter membrane is selected from silicone fluids and silicone gel.

4. The embolic protection system as claimed in claim 3, wherein the coating for preventing self-adherence between folds of the filter membrane is PDMS (poly dimethyl siloxane) or co-polymers of PDMS and PEO (polyethylene oxide) and/or PPO (polypropylene oxide).

5. A system as claimed in claim 1, wherein in the collapsed configuration, the filter membrane is at least partially folded.

6. A system as claimed in claim 5, wherein the coating for preventing self-adherence between folds of the filter membrane substantially prevents adhesion of adjacent folds of the filter membrane to one another in the collapsed configuration.

7. A system as claimed in claim 6, wherein the adhesion preventer is applied to an outer surface of the filter membrane.

8. A system as claimed in claim 1, wherein the embolic protection filter comprises a collapsible body defined by the filter membrane and a support structure to support the body in the expanded configuration.

9. A system as claimed in claim 8, wherein the collapsible body is located at least partially externally of the support structure.

10. A system as claimed in claim 8, wherein adjacent folds of the filter membrane are spaced-apart by one or more arms for extending between adjacent folds of the filter membrane.

11. A system as claimed in claim 10, wherein the support structure comprises the arm.

12. A system as claimed in claim 10, wherein the arm is provided by a tool which is suitable to assist loading of the device into a catheter.

13. A system as claimed in claim 1, wherein the filter membrane has a biocompatible surface.

14. A system as claimed in claim 13, wherein the biocompatible surface is provided as a coating of biocompatible material on the filter.

15. A system as claimed in claim 14, wherein the biocompatible material is a hydrophilic coating.

16. A system as claimed in claim 13, wherein the biocompatible surface is provided on an external surface of the filter.

17. A system as claimed in claim 13, wherein the biocompatible surface is provided on an internal surface of the filter.

18. The embolic protection system as claimed in claim 1, wherein the coating for preventing self-adherence between folds of the filter membrane is a silicone fluid with a viscosity of from 5,000 to 10,000 centipoise.

19. The embolic protection system as claimed in claim 1, wherein the coating for preventing self-adherence between folds of the filter membrane is a silicone fluid with a viscosity of from 1 to 100 centipoise.

20. A method for providing embolic protection during a vascular procedure comprising:
   providing the embolic protection system as claimed in claim 1;
   opening the pouch; and
   removing the delivery catheter containing the embolic protection filter in the collapsed configuration from the pouch.

21. A method as claimed in claim 20 further comprising flushing the filter in the collapsed configuration within the delivery catheter.

22. A method as claimed in claim 21, wherein the filter is flushed prior to sealing of the pouch.

23. A method as claimed in claim 21, wherein the filter is flushed after removal of the delivery catheter containing the filter in the collapsed configuration from the pouch.

24. A method as claimed in claim 20 further comprising loading the delivery catheter and filter onto a guidewire.

25. A method as claimed in claim 24, wherein the delivery catheter and filter are loaded onto a guidewire after removal of the delivery catheter containing the filter in the collapsed configuration from the pouch.

26. A method as claimed in claim 20 comprising loading the delivery catheter and filter into a guide catheter.

27. A method as claimed in claim 26, wherein the delivery catheter and filter are loaded into a guide catheter after removal of the delivery catheter from the pouch.

28. A method as claimed in claim 20 further comprising advancing a guidewire through a vasculature; crossing a desired treatment location with the guidewire; advancing the delivery catheter and filter over the guidewire to deliver the filter to a desired location; and deploying the filter from the delivery catheter at the desired location.

29. A method as claimed in claim 28 further comprising introducing separate from the embolic protection filter an interventional device over the guidewire to the treatment location for carrying out the interventional procedure, embolic material generated during the treatment procedure being captured by the deployed filter; and withdrawing the filter from the vasculature.

30. A method as claimed in claim 29, wherein the interventional procedure includes a balloon dilation of the stenosis while the filter is deployed.

31. A method as claimed in claim 29, wherein the interventional procedure includes placing a stent at the treatment location while the filter is deployed.

32. A method as claimed in claim 28, wherein the treatment location is a region of stenosis.

33. A method as claimed in claim 28, wherein the guidewire is withdrawn after withdrawal of the filter.

34. A method as claimed in claim 28, wherein the filter is slidably disposed on the guidewire when the filter is in the expanded deployed configuration.

35. A method as claimed in claim 28, wherein the filter is rotatably disposed on the guidewire when the filter is in the expanded deployed configuration.

36. An embolic protection system comprising:
 an embolic protection filter having a collapsed delivery configuration and an expanded deployed configuration, the embolic protection filter comprising a filter membrane supported by a filter support frame;
 in the collapsed configuration, the filter being at least partially folded;
 a layer of biocompatible material on an outer surface of the filter membrane;
 an adhesion preventer on the layer of biocompatible material to substantially prevent adhesion of adjacent folds of the filter to one another in the collapsed configuration;
 a delivery catheter having a reception space, the embolic protection filter being housed in the collapsed configuration in the reception space of the delivery catheter; and
 a sealed sterile pouch housing the delivery catheter containing the filter in the collapsed configuration.

37. The embolic protection system as claimed in claim 36, wherein the biocompatible coating is hydrophilic.

38. The embolic protection system as claimed in claim 37, wherein the adhesion preventer is selected from silicone fluids and silicone gel.

39. A method for providing embolic protection during a vascular procedure comprising the steps of:
 providing the embolic protection system according to claim 36;
 opening the pouch;
 removing the delivery catheter containing the embolic protection filter in the collapsed configuration from the pouch; and
 flushing the filter in the collapsed configuration within the delivery catheter.

* * * * *